US012796689B2

(12) United States Patent
Bui et al.

(10) Patent No.: US 12,796,689 B2
(45) Date of Patent: Nov. 17, 2026

(54) LOW ODOR HIGH LEVEL DISINFECTANT

(71) Applicant: Medivators Inc., Plymouth, MN (US)

(72) Inventors: Huyen Bui, Brooklyn Park, MN (US); Tuan Nguyen, Chaska, MN (US); John Matta, Shoreview, MN (US)

(73) Assignee: Medivators Inc., Minneapolis, MN (US)

( * ) Notice: Subject to any disclaimer, the term of this patent is extended or adjusted under 35 U.S.C. 154(b) by 862 days.

(21) Appl. No.: 17/790,877

(22) PCT Filed: Dec. 16, 2020

(86) PCT No.: PCT/US2020/065190

§ 371 (c)(1),
(2) Date: Jul. 5, 2022

(87) PCT Pub. No.: WO2021/141740

PCT Pub. Date: Jul. 15, 2021

(65) Prior Publication Data

US 2023/0076686 A1 Mar. 9, 2023

Related U.S. Application Data

(60) Provisional application No. 62/957,980, filed on Jan. 7, 2020.

(51) Int. Cl.

| | |
|---|---|
| ***A01N 59/00*** | (2006.01) |
| ***A01N 37/02*** | (2006.01) |
| ***A01N 37/10*** | (2006.01) |
| ***A01N 37/36*** | (2006.01) |
| ***A01N 43/08*** | (2006.01) |
| ***A01N 43/40*** | (2006.01) |
| ***A01P 1/00*** | (2006.01) |
| ***A61L 2/186*** | (2026.01) |
| ***A61L 103/15*** | (2026.01) |

(52) U.S. Cl.

CPC ............. *A01N 59/00* (2013.01); *A01N 37/02* (2013.01); *A01N 37/10* (2013.01); *A01N 37/36* (2013.01); *A01N 43/08* (2013.01); *A01N 43/40* (2013.01); *A01P 1/00* (2021.08); *A61L 2/186* (2013.01); *A61L 2103/15* (2026.01)

(58) Field of Classification Search

None

See application file for complete search history.

(56) References Cited

U.S. PATENT DOCUMENTS

| | | | | |
|---|---|---|---|---|
| 6,472,358 | B1 * | 10/2002 | Richter ................ | C11D 3/2079 510/234 |
| 2010/0159028 | A1 | 6/2010 | Shultz | |
| 2013/0243650 | A1 | 9/2013 | Rovison et al. | |
| 2014/0275267 | A1 | 9/2014 | Beug-Deeb et al. | |
| 2014/0308162 | A1 | 10/2014 | Lange et al. | |
| 2016/0074549 | A1 | 3/2016 | Lei et al. | |
| 2018/0235231 | A1 | 8/2018 | Ahmadpour et al. | |

FOREIGN PATENT DOCUMENTS

| | | | | |
|---|---|---|---|---|
| WO | 2008079999 A1 | 7/2008 | | |
| WO | 20160044607 | 3/2016 | | |
| WO | WO-2016044607 A1 * | 3/2016 | ............. | A01N 25/30 |
| WO | 2016100818 A1 | 6/2016 | | |

OTHER PUBLICATIONS

Eli, Israel Journal of Chemistry, 2008 (Year: 2008).*

International Preliminary Report on Patentability dated Jul. 21, 2022, of International PCT Application No. PCT/US/2020/065190 dated Dec. 16, 2020.

International Search Report and Written Opinion of the International Searching Authority Dated Feb. 17, 2021, of International PCT Application No. PCT/US2020/065190 filed Dec. 16, 2020.

* cited by examiner

*Primary Examiner* — Susan T Tran
*Assistant Examiner* — William Craigo

(57) ABSTRACT

The invention describes stable high level disinfectant compositions with peracetic acid, organic acids, a fatty acid and a surfactant that are useful for the elimination of surface contaminants from a medical device such as an endoscope.

25 Claims, 9 Drawing Sheets

LOW ODOR HIGH LEVEL DISINFECTANT

CROSS REFERENCE TO RELATED APPLICATIONS

This application claims priority and benefit of U.S. Provisional application with Ser. No. 62/957,980, filed Jan. 7, 2020, entitled LOW ODOR HIGH LEVEL DISINFECTANT, which is herein incorporated by reference in its entirety.

FIELD OF THE INVENTION

The invention relates generally to compositions and methods to eliminate, for example, *Clostridioides difficile* and/or *Mycobacterium terrae* from contaminated surfaces such as those associated with medical devices.

BACKGROUND OF THE INVENTION

A perfect disinfectant would offer complete and full microbiological sterilization, without harming humans and useful forms of life, be inexpensive, and non-corrosive. However, ideal disinfectants do not exist. Most disinfectants are also, by nature, potentially harmful (even toxic) to humans or animals.

The choice of disinfectant to be used depends on the particular situation. Some disinfectants have a wide spectrum (kill many different types of microorganisms), while others kill a smaller range of disease-causing organisms but are preferred for other properties (they may be non-corrosive, non-toxic, or inexpensive).

Many medical devices and instruments may be reused on a number of patients. Before a medical device or instrument is used on another patient, the medical device or instrument generally needs to be reprocessed. For example, after an endoscope is used on a patient, a number of steps are required to reprocess the endoscope before that the endoscope can be reused. Included in the steps of reprocessing an endoscope is a disinfecting step using, for example, a liquid disinfectant solution.

Conventionally, liquid disinfectant solutions are prepared as aqueous solutions and are then shipped by a manufacturer to a hospital or other facility. The disinfectant solutions may be shipped as a concentrate which is then diluted at the hospital or other facility to disinfect an endoscope. Alternatively, the disinfectant solutions may be shipped end-user concentrations and then used "as is" for disinfecting. For either the concentrated or the "as is" disinfectant solution most of the shipping cost is due to the water in the solution, not the needed disinfectant.

Apparatus and devices designed for the at least partially automated cleaning and sterilization of medical devices and instruments are known. Antimicrobial solutions adapted for use in such sterilizing devices are also known, but may suffer drawbacks either in terms of storage, handling, corrosiveness, or compromised capability of rapid in situ dissolution of the medical device or instrument.

Endoscopes are reprocessed (cleaned) between uses. However, the endoscope needs to be disinfected such that bacteria, fungi, etc. are not transferred to a patient such that the patient is infected with the bacteria. Two common bacteria associated with endoscopic procedures include, for example but are not limited to, *Clostridium difficile* and/or *Mycobacterium terrae*.

*Clostridium difficile* (*C. difficile*), a Gram-positive bacterium, also known in the art as *Clostridioides difficle*, is the leading cause of antibiotic-associated diarrhea and pseudomembranous colitis. The frequency and severity of outbreaks associated with *C. difficile* infection (CDI) has increased in recent years. The decreased levels of normal microflora in the intestines due to medical treatments such as antibiotic use and chemotherapy, can allow *C. difficile* to colonize and proliferate. In humans, *C. difficile*-associated disease (CDAD) is the most commonly diagnosed cause of hospital-associated and antimicrobial-associated diarrhea. The risk of CDAD has traditionally been higher among elderly patients and those that have undergone hospitalization, gastrointestinal surgery, are immunodeficient, or were exposed to antibiotics. Moreover, severe cases are being more frequently identified in younger patients and those without traditional risk factors. A steep rise in CDI incidents over the past decade is attributed to the emergence of the hypervirulent, and now prevalent strain ribotype 027 (also known as North American pulsotype 1 (NAP1) and BI), causing epidemic outbreaks with increased morbidity, mortality and high relapse rates.

*Mycobacterium terrae* is a slow-growing species of *Mycobacterium*. It is an ungrouped member of the third Runyon (nonchromatogenic mycobacteria). It is known to cause serious skin infections, which are relatively resistant to antibiotic therapy. Further, symptoms of infection include swelling, lesions, and inflammation, and may mimic the symptoms of osteoarthritis. Joints, tendons, lung, gastrointestinal tract, and genitourinary tract can be infected by *Mycobacterium terrae*.

Therefore, a need exists for a disinfectant that is effective in eliminating bacteria, for example, from a surface or a crevice of a medical device, such as an endoscope and/or overcomes one or more of the current disadvantages noted above.

BRIEF SUMMARY OF THE INVENTION

The present invention surprisingly provides compositions comprising hydrogen peroxide; a first organic acid comprising a $C_1$ to a $C_6$ monocarboxylic acid; a second organic acid comprising one or more of an alpha hydroxy acid, a beta hydroxy acid, a $C_2$ to a $C_6$ alkyl or alkylene dicarboxylic acid, an aromatic dicarboxylic acid, a reductone or a heteroaromatic monocarboxylic acid; a third organic acid comprising a heteroaromatic dicarboxylic acid or heteroaromatic tricarboxylic acid; a fatty acid; and a surfactant which are useful as high level disinfecting agents.

In one embodiment, the composition includes hydrogen peroxide, the first organic acid comprises acetic acid, the second organic acid comprises citric acid, the third organic acid comprises a dipicolinic acid, the fatty acid comprises decanoic acid and the surfactant is sodium dodecyl sulfate.

In another embodiment, the composition has a hydrogen peroxide concentration of about 4 wt. % to about 10 wt. %, an acetic acid concentration of about 0.1 wt. % to about 8 wt. %, a citric acid concentration of about 0.5 wt. % to about 10 wt. %, a dipicolinic acid concentration of about 0.1 wt. % to about 0.5 wt. %, a decanoic acid concentration of about 0.01 wt. % to about 5 wt. % and a sodium dodecyl sulfate concentration of about 0.1 wt. % to about 5 wt. %.

In yet another embodiment, the composition(s) include a solvent, and in particular, the solvent is water and is present in an amount sufficient to provide a total composition of 100 wt. %.

The present embodiments also provide for a kit that includes: (a) an enclosed container that includes a removable closure; (b) the composition(s) as described herein, located inside the enclosed container, and, optionally, (c) printed indicia located on the enclosed container instructing how the composition should be used to disinfect and/or sterilize a surface.

The present embodiments also provide for a method of reducing the number of microbes located upon a substrate. In some embodiments, the method includes contacting the substrate with an effective amount of the compositions described herein, for a sufficient period of time, effective to reduce the number of microbes located upon the substrate.

The present embodiments also provide for a method of killing or inhibiting a microorganism. In some embodiments, the method includes contacting the microorganism with an antimicrobially effective amount of the composition described herein, for a sufficient period of time, effective to kill or inhibit the microorganism.

The present embodiments also provide for a method of disinfecting or sterilizing a substrate. In some embodiments, the method includes contacting the substrate with an effective amount of the compositions described herein, for a sufficient period of time, effective to disinfect or sterilize the substrate. The present embodiments also provide for a method of disinfecting or sterilizing a medical device. In some embodiments, a method of disinfecting or sterilizing an endoscopic device is achieved with the use of the compositions described herein.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
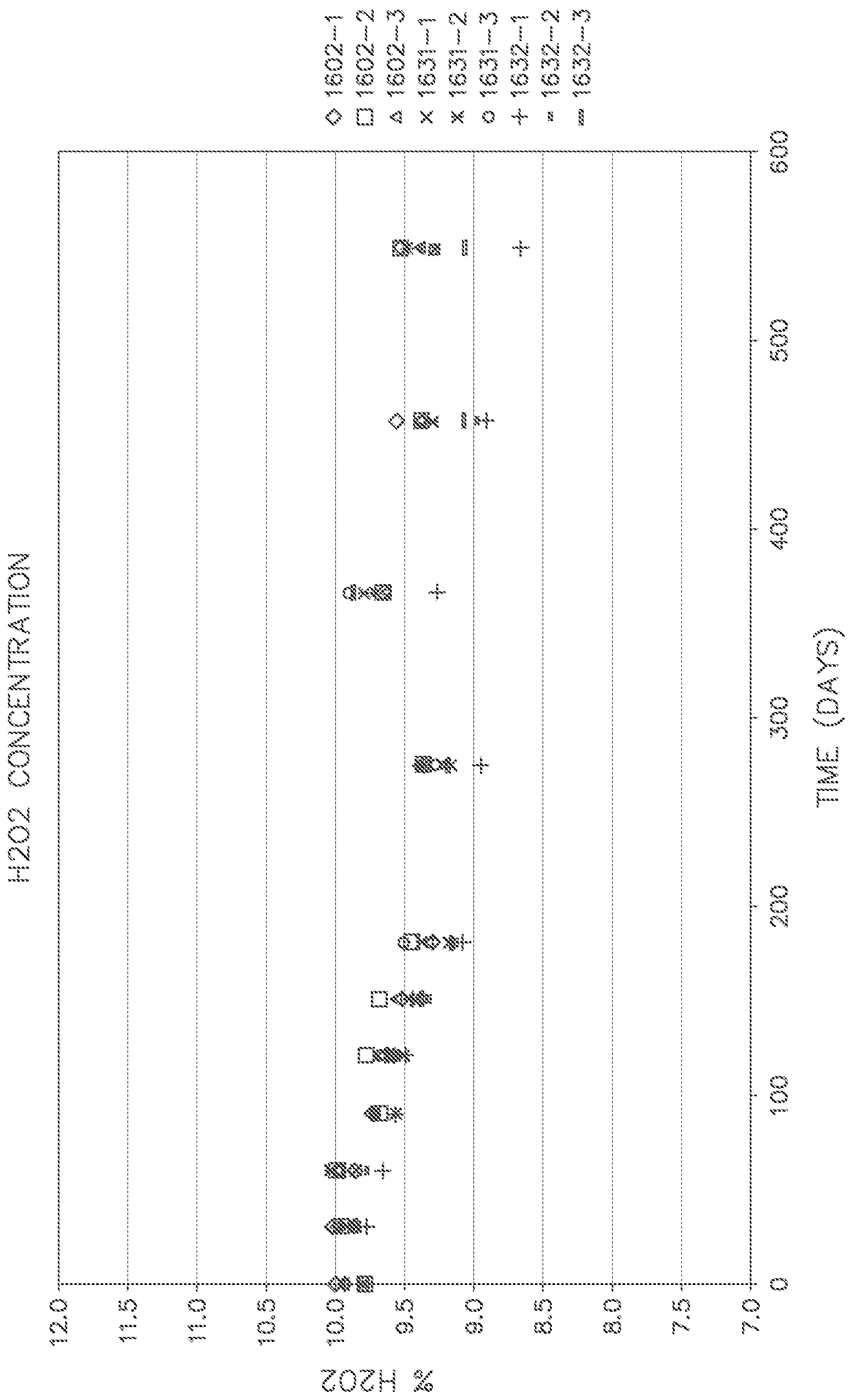
FIG. 1 depicts hydrogen peroxide stability and concentration(s) over 18 months for nine different manufactured lots of the *C. diff* surface disinfectant of Formula 27.
Figure 2:
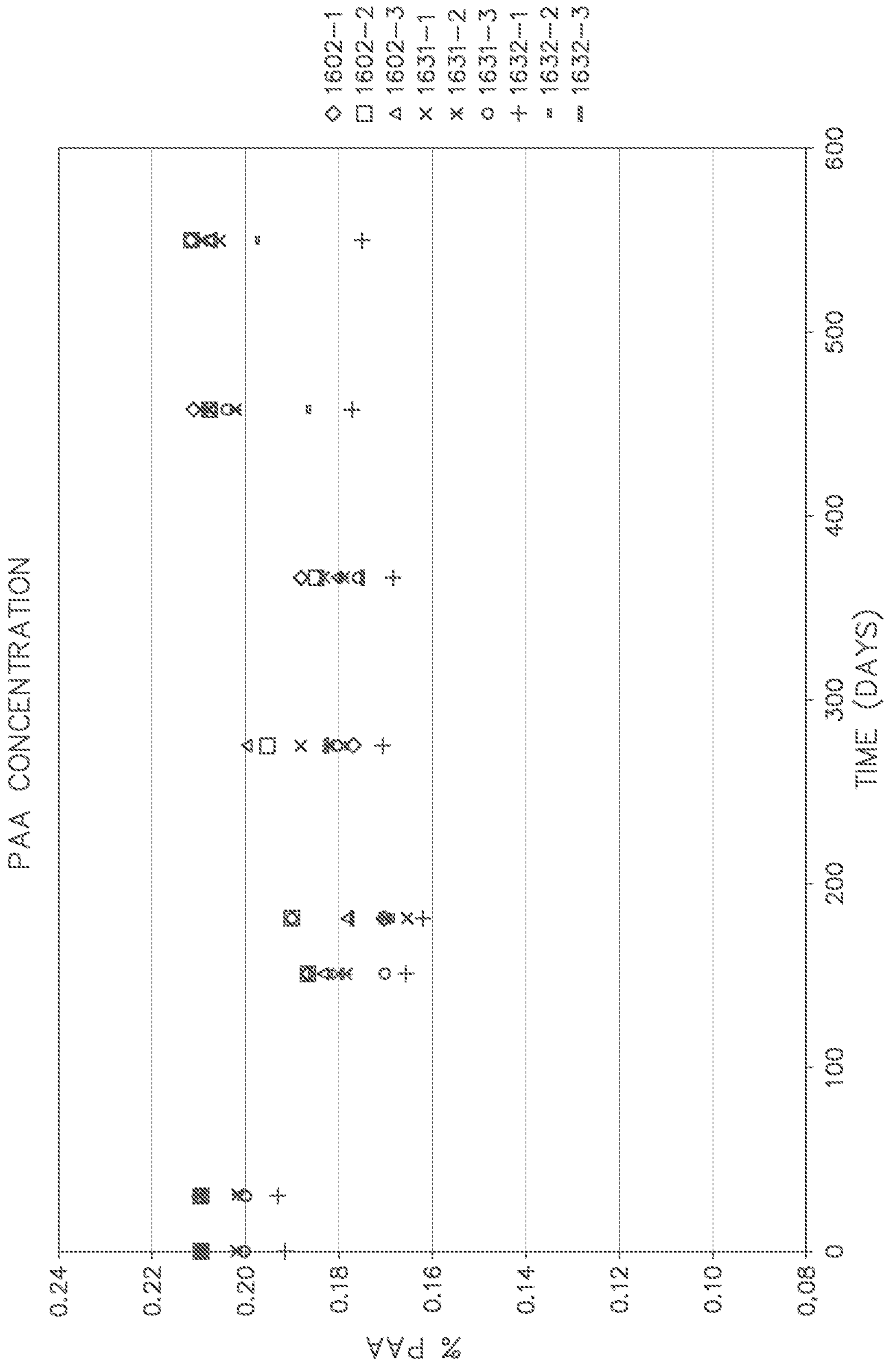
FIG. 2 depicts peracetic acid (PAA) stability and concentration(s) over 18 months for nine different manufactured lots of the *C. diff* surface disinfectant of Formula 27.
Figure 3:
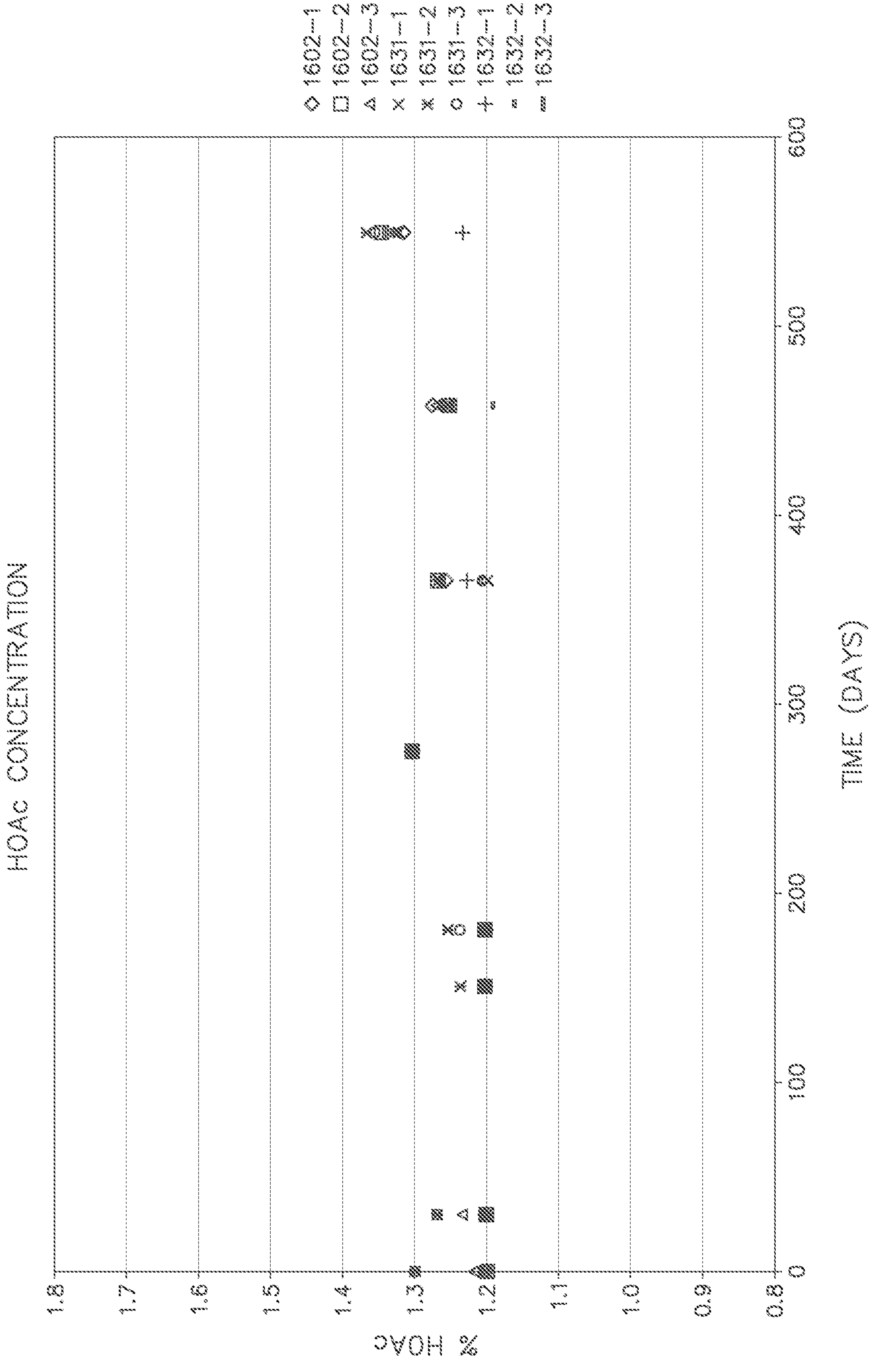
FIG. 3 depicts acetic acid (HOAc) stability and concentration(s) over 18 months for nine different manufactured lots of the *C. diff* surface disinfectant of Formula 27.
Figure 4:
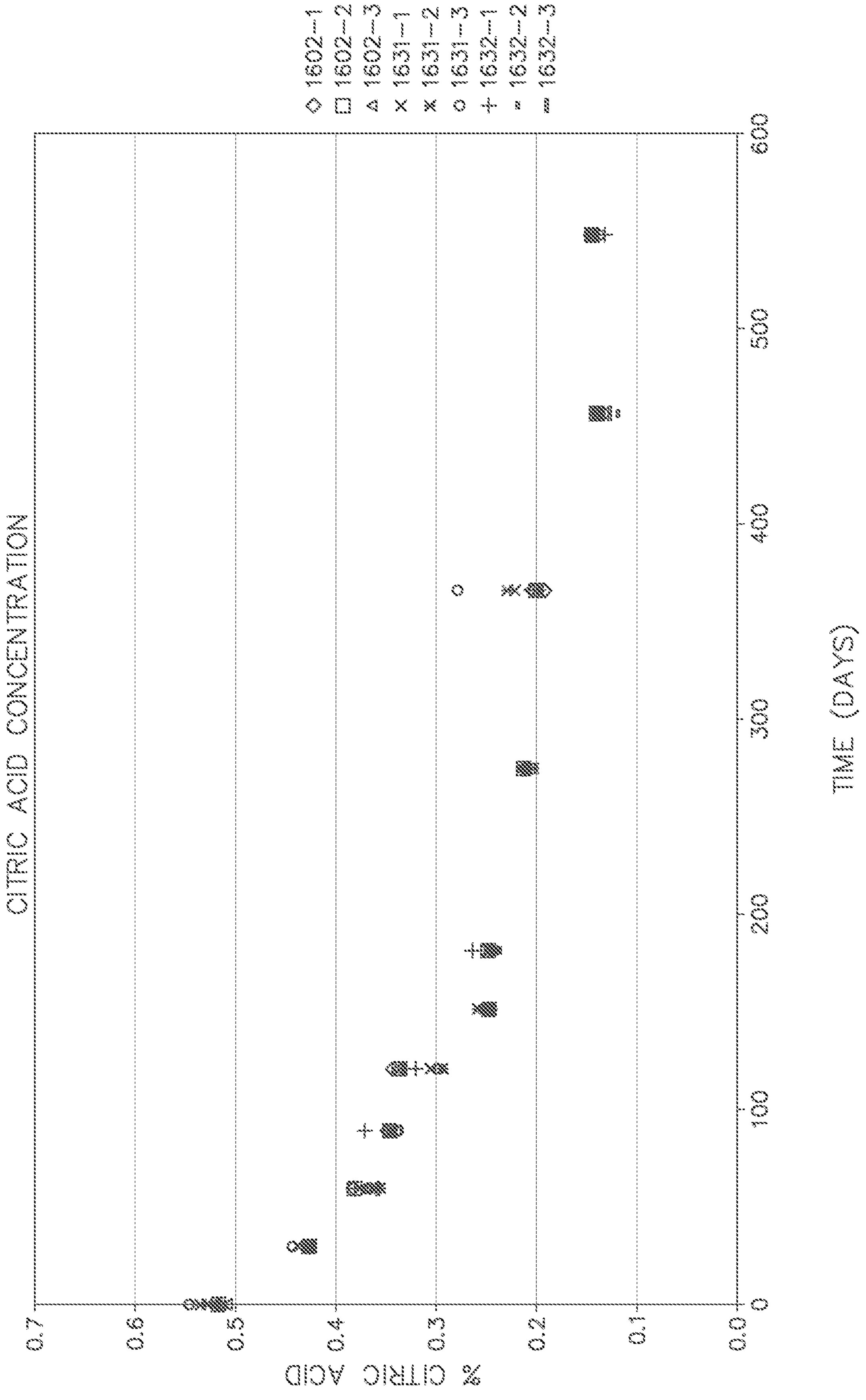
FIG. 4 depicts citric acid stability and concentration(s) over 18 months for nine different manufactured lots of the *C. diff* surface disinfectant of Formula 27.
Figure 5:
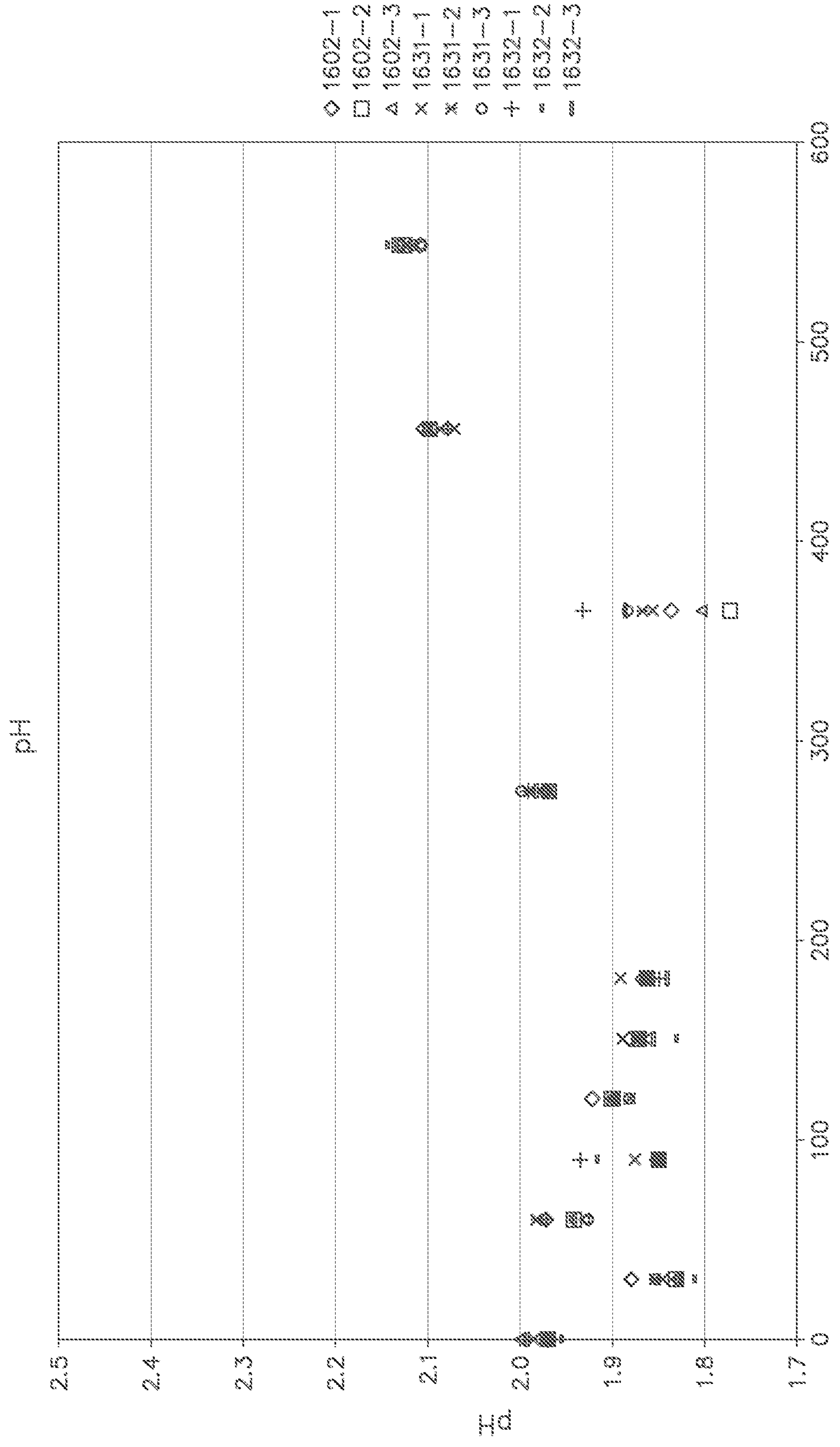
FIG. 5 depicts pH stability and concentration(s) over 18 months for nine different manufactured lots of the *C. diff* surface disinfectant of Formula 27.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" should be interpreted to include not only the explicitly recited amount of about 0.1 wt. % to about 5 wt. %, but also the individual concentrations (e.g., 1%, 2%, 3%, and 4%) and the sub-ranges (e.g., 0.5%, 1.1%, 2.2%, 3.3%, and 4.4%) within the indicated range.

When describing the present invention, the following terms have the following meanings, unless otherwise indicated.

The term "about" can allow for a degree of variability in a value or range, for example, within 10%, within 5%, or within 1% of a stated value or of a stated limit of a range.

The term "room temperature" as used herein refers to a temperature of about 15° C. to 28° C.

The term "hydrogen peroxide" or "$H_2O_2$" refers to the compound chemically designated as dihydrogen dioxide, having the CAS Reg. No. 7722-84-1. In specific embodiments of the invention, the hydrogen peroxide includes water. In further specific embodiments of the invention, the hydrogen peroxide is 50% wt. % hydrogen peroxide in water. The hydrogen peroxide can be present in the composition, in any suitable and effective amount.

The term "organic acid" refers to an organic compound with acidic properties. The most common organic acids are the carboxylic acids, whose acidity is associated with their carboxyl group —COOH. Sulfonic acids, containing the group —$SO_2OH$, are relatively stronger acids. The relative stability of the conjugate base of the acid determines its acidity. Other groups can also confer acidity, usually weakly: —OH, —SH, the enol group, and the phenol group. Organic compounds containing these groups are generally referred to as organic acids. An example of an organic acid is acetic acid.

The phrase "a $C_1$ to a $C_6$ monocarboxylic acid" includes branched and/or unbranched alkyl or alkylene chains with one carboxylic acid present on a $C_1$ to a $C_6$ carbon chain. Suitable examples of $C_1$ to a $C_6$ monocarboxylic acids include, for example but are not limited to, one or more of formic acid, acetic acid, propanoic acid, butanoic acid, sec-butanoic acid, pentanoic acid, pentenoic acid, 2-methylbutanoic acid, 3-methyl butanoic acid, pivalic acid, hexanoic acid, hexenoic acid, hexadienoic acid, etc. as well as their corresponding salts and pharmaceutically-acceptable derivatives, or any combination of any of the foregoing. In particular, the monocarboxylic acid is a branched or unbranched $C_1$ to a $C_3$ monocarboxylic acid.

The term "acetic acid" or "ethanoic acid" refers to an organic compound with the chemical formula $CH_3CO_2H$ (also written as $CH_3COOH$), having the CAS Reg. No. 64-19-7. The term "glacial acetic acid" refers to undiluted and relatively concentrated, water-free (anhydrous) acetic acid.

The phrase "second organic acid" is an agent in addition to, separate and apart from the $C_1$ to a $C_6$ monocarboxylic acid described above. The second organic acid includes one or more of an alpha hydroxy acid, a beta hydroxy acid, a $C_2$ to a $C_6$ alkyl or alkylene dicarboxylic acid, an aromatic dicarboxylic acid, a reductone or a heteroaromatic monocarboxylic acid or any combination of any of the foregoing.

Alpha hydroxy acids are well known in the art. Suitable examples of alpha hydroxy acids include, but are not limited to, glycolic acid, lactic acid, citric acid, malic acid, mandelic acid, tartaric acid alpha-hydroxyethanoic acid, alpha-hydroxyoctanoic acid, alpha-hydroxycaprylic acid, hydroxycaprylic acid, pyuric acid, etc. as well as their corresponding salts and pharmaceutically-acceptable derivatives, or any combination of any of the foregoing.

Beta hydroxy acids are well known in the art. Suitable examples of beta hydroxy acids include, but are not limited to, salicylic acid, substituted salicylic acids, beta hydroxybutanoic acid, tropic acid, or trethocanic acid, etc. as well as their corresponding salts and pharmaceutically-acceptable derivatives, or any combination of any of the foregoing.

The phrase "$C_2$ to a $C_6$ alkyl or alkylene dicarboxylic acid" includes branched and/or unbranched alkyl or alkylene chains with two carboxylic acids present on a $C_2$ to a $C_6$ carbon chain. Suitable examples include, but are not limited to, oxalic acid, malonic acid, succinic acid, glutaric acid, adipic acid, maleic acid, itaconic acid, citraconic acid, mesaconic acid, muconic acid, fumaric acid, etc. as well as their corresponding salts and pharmaceutically-acceptable derivatives, or any combination of any of the foregoing.

The term "aromatic dicarboxylic acid" includes unsubstituted and substituted aromatic rings with two carboxylic acids. Suitable examples include, but are not limited to, phthalic acid, isophthalic acid, terephthalic acid etc., as well as their corresponding salts and pharmaceutically-acceptable derivatives, or any combination of any of the foregoing.

The term "reductone" is recognized in the art. Reductones are enediols with a carbonyl group adjacent to the enediol group, i.e. RC(OH)═C(OH)—C(O)R. Suitable examples include, but are not limited to, ascorbic acid, D-isoascorbic acid, tartronaldehyde, reductic acid, etc., as well as their corresponding salts and pharmaceutically-acceptable derivatives, or any combination of any of the foregoing.

A "heteroaromatic monocarboxylic acid" refers to a heteroaromatic compound with a single carboxylic acid. Suitable examples include, but are not limited to, picolinic acid or substituted picolinic acids, etc., as well as their corresponding salts and pharmaceutically-acceptable derivatives, or any combination of any of the foregoing.

A "heteroaromatic dicarboxylic acid or heteroaromatic tricarboxylic acid" refers to a heteroaromatic compound with two or three carboxylic acid groups present about the heteroaromatic moiety. Suitable example include, but are not limited to, dipicolinic acids, DPAN-oxide (DPA is the abbreviation for dipicolinic acid), 3,4-amino-DPA, 4-chloro-DPA, 4-bis(2-hydroxyethyl)imino-DPA, 3-methyl-DPA, 4-methyl-DPA; furan-2,5-dicarboxylic acid, 4H-pyran-2,6-dicarboxylic acid, 4-methyl-PDC (PDC abbreviation for 4H-pyran-2,6-dicarboxylic acid), 4-pyrone-2,6-dicarboxylic acid (chelidonic acid), pyrazine-2,6-dicarboxylic acid, pyrazinetricarboxylic acid, 6-methylpyrazinoic acid, pyridine-3,5-dicarboxylic acid, pyridine-2,4,6-tricarboxylic acid, pyrimidine-2,4-dicarboxylic acid, 4-hydroxy-DPA (chelidamic acid), 2,4-lutidinic acid, quinolinic acid etc., as well as their corresponding salts and pharmaceutically-acceptable derivatives, or any combination of any of the foregoing.

The phrase "fatty acid" is recognized in the art and includes a carboxylic acid with a long aliphatic chain, which is either saturated or unsaturated. Most naturally occurring fatty acids have an unbranched chain of an even number of carbon atoms, from 4 carbons to 28 carbon, e.g., $C_4$ to $C_{28}$. Fatty acids are generally referred to as either a short chain fatty acid, a medium chain fatty acid, a long chain fatty acid, a very long chain fatty acid, a saturated fatty acid or an unsaturated fatty acid.

Suitable examples of short chain fatty acids (SCFAs) include, but are not limited to, fatty acids with an aliphatic carbon chain of four or five carbons or less (e.g. butyric acid) etc., as well as their corresponding salts and pharmaceutically-acceptable derivatives, or any combination of any of the foregoing. Proprionic acid, butyric acid and valeric acid are considered saturated SCFAs.

Suitable examples of medium chain fatty acids (MCFAs) include, but are not limited to, fatty acids with an aliphatic carbon chain of six (6) to twelve (12) carbons, etc., as well as their corresponding salts and pharmaceutically-acceptable derivatives, or any combination of any of the foregoing. Caproic acid, enanthic acid, caprylic acid, pelargonic acid, capric acid (decanoic acid), undeylic acid and lauric acid are considered saturated MCFAs.

Suitable examples of long chain fatty acids (LCFAs) include, but are not limited to fatty acids with an aliphatic carbon chain of thirteen (13) to twenty one (21) carbons, etc., as well as their corresponding salts and pharmaceutically-acceptable derivatives, or any combination of any of the foregoing. Tridecanoic acid, tetradecanoic acid, pentadecanoic acid, hexadecanoic acid, heptadecanoic acid, octadecanoic acid, nonadecanoic acid, eicosanoic acid, heneicosylic acid are considered saturated LCFAs.

Suitable examples of very long chain fatty acids (VLCFAs) inclue, but are not limited to fatty acids with an aliphatic carbon chain of twenty two (22) or more carbons, etc., as well as their corresponding salts and pharmaceutically-acceptable derivatives, or any combination of any of the foregoing. Docosanoic acid, tricosanoic acid, tetracosanoic acid, pentacosanoic acid, hexacosanoic acid, heptcosanoic acid, octacosanoic acid, nonacosanoic acid, triacontanoic acid, hentriacontanoic acid, dotriacontanoic acid, tritriacontainoic acid, tetratriacontanoic acid, pentatriacontanoic acid, hexatriacontanoic acid, hexatriacontanoic acid, heptatriacontanoic acid and octatriacontanoic acid are considered saturated VLCFAs.

Suitable examples of unsaturated LCFAs and VLCFAs include, but are not limited to, myristoleic acid, palmitoleic acid, sapienic acid, oleic acid, elaidic acid, vaccenic acid, linoleic acid, linolaidic acid, alpha, linolenic acid, arachidonic acid, eicosapentaenoic acid, erucic acid, docosahexaenoic acid, etc., as well as their corresponding salts and pharmaceutically-acceptable derivatives, or any combination of any of the foregoing.

The term "peracetic acid," "peroxyacetic acid," or "PAA" refers to an organic compound with the chemical formula $CH_3CO_3H$.

The term "anticorrosive agent" or "corrosion inhibitor" refers to a compound that, when added to a liquid or gas, decreases the corrosion rate of a material, typically a metal or an alloy. Suitable anticorrosive agents include, e.g., benzotriazole and sodium dodecyl sulfate (SDS).

The term "benzotriazole" or "BTA" refers to the compound 1H-benzotriazole or 1,2,3-benzotriazole, having the CAS Reg. No. 95-14-7.

The term "surfactant" refers to a compound capable of lowering the surface tension of a liquid, the interfacial tension between two liquids, or that between a liquid and a solid. Surfactants may act as detergents, wetting agents, emulsifiers, foaming agents, and/or dispersants. The surfactant can be non-ionic, anionic or cationic. Additionally, the surfactant can include one or more non-ionic surfactants, one or more anionic surfactants, and/or one or more cationic surfactants.

The term "non-ionic surfactant" or "nonionic surfactant" refers to a surfactant, in which the total number of electrons is equal to the total number of protons, giving it a net neutral or zero electrical charge. One suitable class of non-ionic surfactants includes the Pluronic® poloxamers or Tergitol polyglycol ethers available from Dow, such as Tergitol 15-S12 or Tergitol L62.

Poloxamers are nonionic triblock copolymers composed of a central hydrophobic chain of polyoxypropylene (poly (propylene oxide)) flanked by two hydrophilic chains of polyoxyethylene (poly(ethylene oxide)). Poloxamers are also known by the trade name Pluronics®.

Because the lengths of the polymer blocks can be customized, many different poloxamers exist, that have slightly different properties. For the generic term "poloxamer," these copolymers are commonly named with the letter "P" (for poloxamer) followed by three digits, the first two digits "×" (times) 100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic® tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content). In the example given, poloxamer 181 (P181)=Pluronic L61.

The term "Pluronic® 10125 surfactant block copolymer" refers to polyoxypropylene-polyoxyethylene block copolymer, having the CAS Reg. No. 9003-11-6.

Other nonionic surfactants include, but are not limited to, fatty alcohols, polyoxyethylene glycol alkyl ethers (Brij), polyoxypropylene glycol alkyl ethers, glucoside alkyl ethers, polyoxyethylene glycol octylphenol ethers, polyoxyethylene glycol alkylphenol ethers, glycerol alkyl esters, polyoxyethylene glycol sorbitan alkyl esters, sorbitan alkyl esters, cocamide MEAs, cocamide DEAs, dodecyl dimethylamine oxides, block copolymers of polyethylene glycol and polypropylene glycols.

Suitable fatty alcohols include, but are not limited to, cetyl alcohol, stearyl alcohol, cetostearyl alcohol (consisting predominantly of cetyl and stearyl alcohols) and oleyl alcohol.

Suitable polyoxyethylene glycol alkyl ethers, include but are not limited to (Brij), for example $CH_3—(CH_2)_{10-16}—(O—C_2H_4)_{1-25}—OH$, or octaethylene glycol monododecyl ether or pentaethylene glycol monododecyl ether.

Suitable polyoxypropylene glycol alkyl ethers include $CH_3—(CH_2)_{10-16}—(O—C_3H_6)_{1-25}—OH$.

Suitable glucoside alkyl ethers include $CH_3—(CH_2)_{10-16}—(O\text{-Glucoside})_{1-3}\text{-OH}$, and, for example, include decyl glucoside, lauryl glucoside, and octyl glucoside.

Suitable polyoxyethylene glycol octylphenol ethers include $C_8H_{17}—(C_6H_4)—(O—C_2H_4)_{1-25}—OH$. One exemplary material is TRITON X-100.

Suitable polyoxyethylene glycol alkylphenol ethers include $C_9H_1—(C_6H_4)—(O—C_2H_4)_{1-25}—OH$. One example is Nonoxynol-9.

In one aspect, a suitable glycerol alkyl ester is glyceryl laurate.

In another aspect, a suitable polyoxyethylene glycol sorbitan alkyl ester is polysorbate.

In still another aspect, suitable sorbitan alkyl esters are referred to as SPAN, e.g., SPAN-20, sorbitan monolaurate.

The term "cationic surfactant" refers to a surfactant, in which the total number of electrons is less than the total number of protons, giving it a net positive electrical charge.

One kind of cationic surfactant is typically based on pH-dependent primary, secondary or tertiary amines. The primary amines become positively charged at a pH<10, and the secondary amines become charged at a pH<4. One example is octenidine dihydrochloride.

Another type of cationic surfactant is based on permanently charged quaternary ammonium cations, such as alkyltrimethylammonium salts. These include but are not limited to cetyl trimethylammonium bromide (CTAB), hexadecyl trimethyl ammonium bromide, cetyl trimethylammonium chloride (CTAC), cetylpyridinium chloride (CPC), polyethoxylated tallow amine (POEA), benzalkonium chloride (BAC), benzethonium chloride (BZT), 5-Bromo-5-nitro-1,3-dioxane, dimethyldioctadecylammonium chloride and dioctadecyldimethylammonium bromide (DODAB).

The term "anionic surfactant" refers to a surfactant in which the total number of electrons is greater than the total number of protons, giving it a net negative electrical charge. One suitable anionic surfactant is sodium lauryl sulfate.

Anionic surfactants have a permanent anion, such as a sulfate, sulfonate or phosphate anion associated with the surfactant or has a pH-dependent anion, for example, a carboxylate.

Sulfates can be alkyl sulfate or alkyl ether sulfates.

Suitable alkyl sulfates include, but are not limited to, ammonium lauryl sulfate, sodium dodecyl sulfate (SDS), or sodium lauryl sulfate (SLS). Suitable alkyl ether sulfates include, but are not limited to, sodium laureth sulfate, also known as sodium lauryl ether sulfate (SLES) or sodium myreth sulfate.

Suitable sulfonates include, but are not limited to, docusate (dioctyl sodium sulfosuccinate), fluorosurfactants that are sulfonated and alkyl benzene sulfonates.

Typical sulfonated fluorosurfactants include, but are not limited to, perfluorooctanesulfonate (PFOS) or perfluorobutanesulfonate.

Phosphates are typically alkyl aryl ether phosphates or alkyl ether phosphates.

Carboxylates are typically alkyl carboxylates, such as fatty acid salts (soaps), such as for example, sodium stearate. Alternatively, the carboxylate can be, but is not limited to, sodium lauryl sarcosinate. In another alternative aspect, the carboxylate includes but is not limited to a carboxylated fluorosurfactant, such as perfluorononanoate, or perfluorooctanoate (PFOA or PFO).

When a single surfactant molecule exhibits both anionic and cationic dissociations it is called amphoteric or zwitterionic. Zwitterionic (amphoteric) surfactant is based on primary, secondary or tertiary amines or quaternary ammonium cation also having a sulfonate, carboxylate or a phosphate.

Suitable zwitterionic surfactants include, but are not limited to, CHAPS (3-[(3-Cholamidopropyl)dimethylammonio]-1-propanesulfonate) or a sultaine. The sultaine is typically cocamidopropyl hydroxysultaine.

In one aspect, the carboxylate cation is an amino acid, imino acid or betaine. In one aspect, the betaine is typically cocamidopropyl betaine.

When the zwitterionic surfactant includes a phosphate, lecithin is often chosen as the counterion.

The term "sodium dodecyl sulfate," "SDS," "NaDS," "sodium lauryl sulfate," or "SLS" refers to an organic compound with the formula $CH_3(CH_2)_{11}OSO_3Na$), having the CAS Reg. No. 151-21-3.

The term "disinfectant" refers to a substance that when applied to non-living objects, destroys microorganisms that are living on the objects. The term "disinfect" refers to the process of destruction or prevention of biological contaminants. Disinfection does not necessarily kill all microorganisms, especially nonresistant bacterial spores; it is less effective than sterilization, which is an extreme physical and/or chemical process that kills all types of life.

Disinfectants are different from other antimicrobial agents such as antibiotics, which destroy microorganisms within the body, and antiseptics, which destroy microorganisms on living tissue. Disinfectants are also different from biocides. The latter are intended to destroy all forms of life, not just microorganisms. Sanitizers are substances that simultaneously clean and disinfect.

The term "sterilant" (via sterilization) refers to a substance that when applied to non-living objects, destroys all viable forms of microbial life, when used according to labeling.

The term "CFU" refers colony forming units and is a measure of viable cells in which a colony represents an aggregate of cells derived from a single progenitor cell.

In various embodiments, the compositions described herein can include a chelator, also referred to as a "stabilizer".

The term "chelator," "chelant" or "chelating agent" refers to a compound that forms soluble, complex molecules with certain metal ions, inactivating the metal ions (or to some extent, countering the effects of the metal ions), so that they cannot normally react with other compounds, elements or ions. In specific embodiments, the chelator effectively chelates transition metals. One suitable type of chelator is/are sulfonic acids, more particularly, polymers or solid supports which contain sulfonic acid functionality. In specific embodiments, the chelator will effectively chelate any transition metals and/or alkaline earth metals present in any of the components of the composition.

In particular, the chelator can be a sulfonic acid group that is incorporated into a polymer. For example, the polymer can be styrene based that is functionalized with sulfonic acid groups. The styrenic polymer can be a copolymer, such as styrene/divinylbenzene. The polymer may further be crosslinked. Examples of commercially available sulfonic acid functionalized polymers include those such as Dowex® 50WX4-200, Dowex® DR2030, Amberlite IR120 Na, Amberlite IRN99, Amberlyst 15 hydrogen (CAS Number 39389-20-3) and Amberlite strong acidic cation exchange sodium form available from Dow Chemical Company, which are styrene-divinylbenzene copolymers.

Alternatively, a copolymer of tetrafluoroethylene (TFE) and Sulfonyl Fluoride Vinyl Ether (SFVE) $F_2C{=}CF{-}O{-}CF_2CF_2{-}SO_2F$ is a useful material. Aquivion® PFSA (perfluorosulfonic acid) ionomers, available from Solvay, are based on this copolymer or tetrafluoroethylene-perfluoro(3-oxa-4-pentenesulfonic acid) copolymers (e.g., $[CF_2CF(OCF_2CF_2SO_3H)]_m[CF_2CF_2]_n$, as Aquivion E98-15S, Aquivion E98-09S, Aquivion PW79S, or Aquivion E87-05S available from Sigma or Krackeler Scientific, Inc.). and are available in a membrane, as a powder, in a dispersion or as pellets. These are all perfluorosulfonic acid resins.

In one aspect, the perfluorosulfonic acid pellets can be extruded/coextruded with other polymers to form films or shaped into a container to hold the remaining components of the embodiments. Suitable extrusion polymers include, for example, polyethylenes, e.g., (high density polyethylene, HDPE) and polypropylenes.

In another embodiment, the polymer can be derived from 2-acrylamido-2-methylpropane sulfonic acid (AMPS). Additionally, AMPS can be used to coat the lining of a container and then be polymerized to the surface of the container as a protective/chelating coating.

It should be understood that the requisite sulfonic acid group may need to be first treated with an acidic solution to provide the free acid as necessary.

The polymeric resin chelator can be added to the compositions described herein. Alternatively, the compositions can be passed through the polymeric resin chelator. In another embodiment, the polymeric resin chelator can be in the form of a membrane and the membrane is in contact and remains in contact with the composition. In still another embodiment, the polymeric resin chelator is incorporated into a container which hold the compositions described herein. In certain embodiments, the polymer resin chelator is coated onto the interior of a container that is used to store the compositions described herein. In still another embodiment, the polymeric chelator can be placed within a "mesh pouch" or other containment system that can be placed into a container with the compositions described herein.

One advantage of utilizing the polymeric resin chelator is that users of the compositions often contaminate the composition in between uses. That is, an individual may place a used wipe, sponge, or rag, medical device, instrument, etc. against or within the container that houses the composition, thus transferring contaminants to the container. The polymeric resin chelators described herein help to stabilize the peracetic acid/hydrogen peroxide compositions by complexing with/removing the undesired contaminants, such as metal ions.

It should be understood that one advantage of the polymeric resin chelator is that it does not dissolve in the embodiments described herein. That is, the polymer resin remains in the solution but does not become homogeneous with the remaining components. Not to be limited by theory, it is believed that the polymeric resin chelator provides surface contact with the components of the composition and removes metallic contaminants from the solution to stabilize the composition. As a result, the components of the composition, e.g., the hydrogen peroxide and/or the peracetic acid, do not degrade over time due to metallic components. Additionally, the polymeric resin chelator does not cause a residue to remain on a treated surface after the surface has been treated with the compositions described herein.

In certain aspects of the embodiments, a chelator or stabilizer is not required and is not included in the composition.

In certain aspects, the peracetic acid/hydrogen peroxide compositions are stabilized without the need for a phosphonic based chelator, such as 1-hydroxyethylidene-1,1-diphosphonic acid. In other aspects, a phosphonic based chelator, such as 1-hydroxyethylidene-1,1-diphosphonic acid can be included in the sterilant fluid and therefore, component c), the polymeric sulfonic acid resin is optional.

In embodiments disclosed herein, the compositions and methods do not leave a residue on a treated surface after use of the composition to treat the surface.

The use of the polymeric stabilizer/chealtor is detailed in pending PCT application PCT/US2019/053090, filed Sep. 26, 2019, entitled "Peracetic Acid Stabilized Compositions with Polymeric Resins Chelators", the contents of which are incorporated herein by reference.

It is appreciated that those of ordinary skill in the art fully understand and appreciate that when a composition includes more than one component, the composition may also include additional components formed as a product of the reaction between the components in the composition. For example, those of skill in the art fully understand and appreciate that a composition including hydrogen peroxide ($H_2O_2$) and acetic acid ($CH_3CO_2H$) also includes the oxidized product of acetic acid, peracetic acid ($CH_3CO_3H$). As such, reference to the composition including hydrogen peroxide ($H_2O_2$) and acetic acid ($CH_3CO_2H$) is proper, as well as reference to the composition being formed from hydrogen peroxide ($H_2O_2$) and acetic acid ($CH_3CO_2H$). To that end, a composition of acetic acid and hydrogen peroxide will include significant and appreciable amounts of peracetic acid formed from the reaction of acetic acid with hydrogen peroxide. Further, it is appreciated that those of ordinary skill in the art fully understand and appreciate that an equilibrium exists between hydrogen peroxide and acetic acid, and peracetic acid.

In various embodiments of the compositions described herein, peracetic acid is present in about 0.1 wt. % to about 1 wt. % of the composition. In some embodiments, peracetic acid is present in about 0.1-1 wt. %, 0.2-0.9 wt. %, 0.3-0.8 wt. %, 0.4-0.7 wt. %, about 0.5-0.6 wt. % of the composition. In some embodiments, peracetic acid is present in about 0.4 wt. % to about 0.6 wt. %, e.g. 0.5 wt. % of the composition.

In various embodiments of the compositions described herein, hydrogen peroxide is present in about 0.5 wt. % to about 40 wt. % of the composition. In some embodiments (e.g., before equilibration and formation of PAA), the hydrogen peroxide is present in about 0.5-35 wt. %, 1-20 wt. %, or about 2-15 wt. % of the composition. In some embodiments (e.g., after equilibration and formation of PAA), the hydrogen peroxide is present in about 3-30 wt. %, 4-15 wt. %, 5-10 wt. % or about 2-15 wt. % of the composition. In some embodiments, the hydrogen peroxide is present in about 1 wt. %, 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, or about 17 wt. %. In some embodiments, the hydrogen peroxide is about 35 wt. % in water, present in about 0.5 wt. % to about 40 wt. % of the composition. In some embodiments, hydrogen peroxide is about 35 wt. % in water, present in about 1 wt. % of the composition. In some embodiments, hydrogen peroxide is about 35 wt. % in water, present in about 10 wt. % to about 40 wt. % of the composition.

In various embodiments, the first organic acid(s) of the compositions described herein, a $C_1$ to a $C_6$ monocarboxylic acid, includes acetic acid. In some embodiments, the organic acid comprises glacial acetic acid. In some embodiments, the organic acid includes acetic acid, present in at least about 1 to about 1.5 wt. % of the composition. In some embodiments (e.g., before equilibration and formation of PAA), the organic acid includes acetic acid, present in about 0.1-55 wt. %, 2-45 wt. %, 3-40 wt. %, 4-35 wt. %, 6-30 wt. %, 8-24 wt. %, 10-22 wt. %, 12-20 wt. %, about 14-18 wt. %, or about 0.9 wt. %, 1 wt. %, 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, or 2 wt. % of the composition. In some embodiments (e.g., after equilibration and formation of PAA), the organic acid includes acetic acid, present in about 0.1-5 wt. %, 0.5-2 wt. %, 1-2 wt. %, 1.1-2 wt. %, 1.2-2 wt. %, 1.3-2 wt. %, 1.4-2 wt. %, 1 wt. %, or about 1.5 wt. % of the composition.

In various embodiments, the second organic acid(s) of the compositions disclosed herein, comprises one or more of an alpha hydroxy acid, a beta hydroxy acid, a $C_2$ to a $C_6$ alkyl or alkylene dicarboxylic acid, an aromatic dicarboxylic acid, a reductone or a heteroaromatic monocarboxylic acid, such as citric acid. In some embodiments (e.g., before equilibration and formation of PAA), the second organic acid includes, for example, citric acid, present in about 0.1-20 wt. %, 0.5-20 wt. %, 1-20 wt. %, 2-20 wt. %, 3-20 wt. %, 4-20 wt. %, 5-20 wt. %, 6-20 wt. %, about 7-18 wt. %, or about 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 2 wt. %, 3 wt. %, 4 wt. %, 5 wt. %, 6 wt. %, 7 wt. %, 8 wt. %, 9 wt. %, 10 wt. %, 11 wt. %, 12 wt. %, or about 55 wt. % of the composition. In some embodiments (e.g., after equilibration and formation of PAA), the second organic acid is present in about 0.1-20 wt. %, 0.5-18 wt. %, 1-17 wt. %, 4-16 wt. %, 5-15 wt. %, 6-14 wt. %, 7-13 wt. %, 8-12 wt. %, or about 9-11 wt. % of the composition. In some embodiments, the second organic acid is present in about 0.2 wt. % to about 1 wt. % of the composition. In some embodiments, the second organic acid is present in about 0.5 wt. % of the composition.

In various embodiments, the third organic acid(s) of the compositions disclosed herein, comprises a heteroaromatic dicarboxylic acid, such as dipicolinic acid. In some embodiments (e.g., before equilibration and formation of PAA), the third organic acid includes, for example, dipicolinic acid, present in about 0.05-2 wt. %, 0.05-2 wt. %, 0.075-2 wt. %, 0.1-2 wt. %, 0.15-2 wt. %, 0.2-2 wt. %, 0.3-2 wt. %, 0.4-2 wt. %, 0.5-2 wt. %, 0.6-2 wt. %, 0.7-2 wt. %, 0.8-2 wt. %, 0.9-2 wt. %, 1-2 wt. %, 1.1-2 wt. %, 1.2-2 wt. % through and including 1.9-2 wt. % of the composition. In some embodiments (e.g., after equilibration and formation of PAA), the third organic acid is present in about 0.1-1 wt. %, 0.1-0.9 wt. %, 0.1-0.8 wt. %, 0.1-0.7 wt. %, 0.1-0.6 wt. %, 0.1-0.5 wt. %, 0.1-0.4 wt. %, 0.1-0.3 wt. %, or about 0.1-0.2 wt. % of the composition. In some embodiments, the third organic acid is present in about 0.1 wt. % to about 0.5 wt. % of the composition. In some embodiments, the third organic acid is present in about 0.5 wt. % of the composition.

In certain aspects, the fatty acid(s) of the compositions disclosed herein include decanoic acid. In some embodiments (e.g., before equilibration and formation of PAA), the fatty acid includes, for example, decanoic acid, present in about 0.01-5 wt. %, 0.05-2 wt. %, 0.075-2 wt. %, 0.1-5 wt. %, 0.15-5 wt. %, 0.2-5 wt. %, 0.3-5 wt. %, 0.4-5 wt. %, 0.5-5 wt. %, 0.6-5 wt. %, 0.7-5 wt. %, 0.8-5 wt. %, 0.9-5 wt. %, 1-5 wt. %, 1.1-5 wt. %, 1.2-5 wt. % through and including 1.9-5 wt. % of the composition. In some embodiments (e.g., after equilibration and formation of PAA), the fatty acid is present in about 0.1-5 wt. %, 0.1-0.9 wt. %, 0.1-0.8 wt. %, 0.1-0.7 wt. %, 0.1-0.6 wt. %, 0.1-0.5 wt. %, 0.1-0.4 wt. %, 0.1-0.3 wt. %, or about 0.1-0.2 wt. % of the composition. In some embodiments, the fatty acid is present in about 0.01 wt. % to about 0.5 wt. % of the composition. In some embodiments, the fatty acid is present in about 0.5 wt. % of the composition.

In certain aspects, the surfactant(s) of the compositions disclosed herein include an alkyl sulfate, such as sodium dodecyl sulfate (SDS). In some embodiments (e.g., before equilibration and formation of PAA), the surfactant includes, for example, SDS, present in about 0.1-10 wt. %, 0.2-10 wt. %, 0.5-10 wt. %, 1-10 wt. %, 2-10 wt. %, 3-10 wt. %, 4-10 wt. %, 5-10 wt. %, 6-10 wt. %, 7-10 wt. %, 8-10 wt. %, 9-10 wt. %, 0.1-3 wt. %, 0.1-2 wt. %, 0.1-3 wt. %, 0.1 wt. % through and including 1.9-5 wt. % of the composition. In some embodiments (e.g., after equilibration and formation of PAA), the surfactant is present in about 0.1-5 wt. %, 0.1-0.9 wt. %, 0.1-0.8 wt. %, 0.1-0.7 wt. %, 0.1-0.6 wt. %, 0.1-0.5 wt. %, 0.1-0.4 wt. %, 0.1-0.3 wt. %, or about 0.1-0.2 wt. % of the composition. In some embodiments, the surfactant is present in about 0.1 wt. % to about 1 wt. % of the composition. In some embodiments, the surfactant is present in about 0.5 wt. % of the composition.

In various embodiments, the composition(s) include hydrogen peroxide, the first organic acid comprising a $C_1$ to a $C_6$ monocarboxylic acid comprises acetic acid, the second organic acid comprises citric acid, the third organic acid comprises a dipicolinic acid, the fatty acid comprises decanoic acid and the surfactant is sodium dodecyl sulfate.

In one aspect, the composition comprises a hydrogen peroxide concentration of about 4 wt. % to about 10 wt. %, the acetic acid concentration is at about 0.1 wt. % to about 8 wt. %, the citric acid concentration is about 0.5 wt. % to about 10 wt. %, the dipicolinic acid concentration is about 0.1 wt. % to about 0.5 wt. %, the decanoic acid concentration is about 0.1 wt. % to about 5 wt. % and the sodium dodecyl sulfate concentration is about 0.1 wt. % to about 5 wt. %.

In specific embodiments, the composition of the present invention can be formulated as, can exist as, and can be commercially available as a liquid concentrate disinfectant or sterilant. The term "liquid concentrate" refers to a composition that is relatively undiluted and concentrated, having a low content of carrier, e.g., water. Having the composition be commercially available as a liquid concentrate will typically save costs associated with the manufacturing, shipping, and/or storage of the product.

When the composition of the present invention is formulated as a liquid concentrate, the concentrate can subsequently be diluted with an appropriate amount of carrier (e.g., water) prior to use. Additionally, although considered to be a concentrate, when the composition of the present invention is formulated as a liquid concentrate, a discrete and finite amount of carrier (e.g., water) can be employed.

The compositions of the present invention can be formulated for application, depending upon the user's preference as well as the ultimate application of the composition. For example, the composition can be formulated for use in a sprayable composition, atomized liquid sprayer, or liquid applicator. Such formulations can include at least one of a spray bottle, motorized sprayer, wipe, cloth, sponge, non-woven fabric, and woven fabric. Such formulations may be particularly suitable for applying the composition to a surface of a hospital, physician's office, medical clinic, medical facility, dental office, dental facility, airport, school, pet store, zoo, children's day care, elderly nursing home, museum, movie theatre, athletic facility, sporting arena, gymnasium, rest room, bathroom, shopping center, amusement park, church, synagogue, mosque, temple, restaurant, food processing facility, food manufacturing facility, pharmaceutical company, hot-tub, sauna, and/or clean room.

Such liquid formulations may be particularly suitable for applying the composition to metal, plastic, natural rubber, synthetic rubber, glass, stone, grout, fiberglass, wood, concrete, construction products, and/or building products.

In various embodiments, the composition of the invention can be configured for use in contacting at least one of medical equipment, medical device (e.g., reusable medical device or instrument, such as an endoscope), surface in the medical industry, dental equipment, dental device, and surface in the dental industry. In some embodiments, the composition of the invention may be used in the reconditioning of a soiled endoscopic device. In some embodiments, the compositions of the invention are useful during the disinfection step or sterilization step of the high level disinfection cleaning process following use of the endoscope in a medical procedure. The term "endoscopic device" includes a plurality of minimally invasive surgical devices (e.g., scopes) that have been developed for specific uses. For example, upper and lower endoscopes are utilized for accessing the esophagus/stomach and the colon, respectively, angio scopes are utilized for examining blood vessels, and laparoscopes are utilized for examining the peritoneal cavity.

In some embodiments, catalysts for the formation of peracetic acid from hydrogen peroxide and acetic acid are employed. Suitable catalysts include, for example, inorganic acids, such as sulfuric acid ($H_2SO_4$), hydrochloric acid (HCl), phosphoric acid ($H_3PO_4$), and nitric acid ($HNO_3$).

In specific embodiments, the composition of the present invention can be non-corrosive. The term "non-corrosive" or "noncorrosive" refers to a substance that will not destroy or irreversibly damage another surface or substance with which it comes into contact. The main hazards to people include damage to the eyes, the skin, and the tissue under the skin; inhalation or ingestion of a corrosive substance can damage the respiratory and gastrointestinal tracts. Exposure results in chemical burn. Having the composition be relatively non-corrosive will allow the user to employ the composition over a wider range of uses, exposing the composition to a wider range of substrates. For example, having the composition be relatively non-corrosive will allow the user to employ the composition as a disinfectant or sterilant with certain medical devices that are highly sensitive to corrosive substances.

In specific embodiments, the composition of the present invention can be non-toxic. The term "non-toxic" refers to a substance that has a relatively low degree to which it can damage a living or non-living organism. Toxicity can refer to the effect on a whole organism, such as an animal, bacterium, or plant, as well as the effect on a substructure of the organism, such as a cell (cytotoxicity) or an organ (organotoxicity), such as the liver (hepatotoxicity). A central concept of toxicology is that effects are dose-dependent; even water can lead to water intoxication when taken in large enough doses, whereas for even a very toxic substance such as snake venom there is a dose below which there is no detectable toxic effect. Having the composition be relatively non-toxic will allow a wider range of users be able to safely handle the composition, without serious safety concerns or risks.

In specific embodiments, the composition of the present invention can be stable over extended periods of time (i.e., has a long-term stability). The term "long-term stability" refers to a substance undergoing little or no physical and/or chemical decomposition or degradation, over extended periods of time.

In further specific embodiments, the composition of the present invention can be stable over extended periods of time, such that at about 1 atm and about 19° C., less than about 20 wt. %, e.g., 15 wt. %, 10 wt. %, or 5 wt. %, of each component independently degrades over about one year. In additional specific embodiments, the composition of the present invention can be stable over extended periods of time, such that at about 1 atm and about 19° C., at least about 80 wt. % of each component, e.g., 85 wt. %, 90 wt. %, 95 wt. %, is independently present after about one year.

Having the composition be relatively stable over extended periods of time will allow the composition to retain its effectiveness over that time, ensuring that it will remain useful and active for its intended purpose. In contrast, in those compositions that do not retain their effectiveness over that time, product loss can result, which can be financially costly. Additionally, risks associated with the use of a product that has lost some or all of its effectiveness for the intended purpose can be hazardous, in that the product may not effectively achieve the desired goal. For example, when used to disinfect or sterilize a medical device, use of a composition that has lost some or all of its effectiveness as a disinfectant or sterilant may not effectively disinfect or sterilize the medical device. Medical injuries can be sustained by the patient, including serious infections.

In specific embodiments, the composition of the present invention can be formulated as, can exist as, and is commercially available as, a one-part composition. The term "one-part composition" refers to all chemical components of a composition being present together, such that they are each in intimate and physical contact with one another, and are each present in a single container. Having the composition be commercially available as a one-part composition will be more cost effective (e.g., lower manufacturing costs associated with fewer containers), and will avoid the necessity of the user mixing or combining multiple components together, prior to using.

In specific embodiments, the composition of the present invention can be essentially free of buffer. In further specific embodiments, the composition of the present invention can include less than about 0.1 wt. % buffer. The term "buffer," "buffering agent," or "buffering substance" refers to a weak acid or base used to maintain the acidity (pH) of a solution at a chosen value. The function of a buffering agent is to prevent a rapid change in pH when acids or bases are added to the solution. Buffering agents have variable properties—some are more soluble than others; some are acidic while others are basic.

In specific embodiments, the composition of the present invention can be essentially free of transition metals. In further specific embodiments, the composition of the present invention can include less than about 0.001 wt. % transition metals. In further specific embodiments, the composition of the present invention can include less than about 0.0001 wt. % transition metals. In further specific embodiments, the composition of the present invention can include less than about 0.00001 wt. % transition metals. Having the composition include a minimal amount of transition metals decreases the likelihood that the transition metals will cause degradation and/or decomposition of the composition, over the extended periods of time associates with the manufacturing, shipping, and storage of the composition. This is especially so when the composition is formulated as a concentrated, one-part composition.

The term "transition metal," "transition metals" or "transition element" refers to an element whose atom has an incomplete d sub-shell, or which can give rise to cations with an incomplete d sub-shell. Transition metals include scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), mercury (Hg), rutherfordium (Rf), dubnium (db), seaborgium (Sg), bohrium (Bh), hassium (Hs) and copernicium (Cn).

In specific embodiments of the invention, the transition metal can be naturally occurring. Naturally occurring transition metals include scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), and mercury (Hg).

In specific embodiments, the composition of the present invention can be essentially free of heavy metals. In further specific embodiments, the composition of the present invention can include less than about 0.001 wt. % heavy metals. In further specific embodiments, the composition of the present invention can include less than about 0.0001 wt. % heavy metals. In further specific embodiments, the composition of the present invention can include less than about 0.00001 wt. % heavy metals. Having the composition include a minimal amount of heavy metals decreases the likelihood that the transition metals will cause degradation and/or decomposition of the composition, over the extended periods of time associates with the manufacturing, shipping, and storage of the composition. This is especially so when the composition is formulated as a concentrated, one-part composition.

The term "heavy metal," "heavy metals" or "toxic metal" refers to metals that are relatively toxic, and mainly include the transition metals, some metalloids, lanthanides, and actinides. Examples of toxic metals include, e.g., iron (Fe), cobalt (Co), copper (Cu), manganese (Mn), molybdenum (Mo), zinc (Zn), mercury (Hg), plutonium (Pu), lead (Pb), vanadium (V), tungsten (W), cadmium (Cd), aluminium (Al), beryllium (Be), and arsenic (As).

The present invention also provides for a kit that includes: (a) an enclosed container that includes a removable closure; (b) the composition of the present invention as described herein, which is located inside the enclosed container; and (c) printed indicia located on the enclosed container.

In specific embodiments, the enclosed container can be opaque. In additional specific embodiments, the enclosed container can be manufactured from high density polyethylene (HDPE), thereby providing the requisite opacity. Having the enclosed container be manufactured from high density polyethylene (HDPE) will decrease the likelihood that the composition will degrade and/or decompose over extended periods of time, due to excessive exposure to direct sunlight.

The term "high-density polyethylene" or "HDPE" refers to a polyethylene thermoplastic made from petroleum. The mass density of high-density polyethylene can range from 0.93 to 0.97 g/$cm^3$. Although the density of HDPE is only marginally higher than that of low-density polyethylene, HDPE has little branching, giving it stronger intermolecular forces and tensile strength than LDPE. The difference in strength exceeds the difference in density, giving HDPE a higher specific strength. It is also harder and more opaque and can withstand somewhat higher temperatures (120° C./248° F. for short periods, 110° C./230° F. continuously). HDPE is resistant to many different solvents.

The term "solvent" as used herein refers to a liquid that can dissolve a solid, liquid, or gas. Non-limiting examples of solvents are silicones, organic compounds, water, alcohols, ionic liquids, and supercritical fluids.

The term "opaque" refers to an object that is neither transparent (allowing all light to pass through) nor translucent (allowing some light to pass through). When light strikes an interface between two substances, in general some may be reflected, some absorbed, some scattered, and the rest transmitted (also see refraction). Reflection can be diffuse, for example light reflecting off a white wall, or specular, for example light reflecting off a mirror. An opaque substance transmits no light, and therefore reflects, scatters, or absorbs all of it. Both mirrors and carbon black are opaque. Opacity depends on the frequency of the light being considered. For instance, some kinds of glass, while transparent in the visual range, are largely opaque to ultraviolet light. More extreme frequency-dependence is visible in the absorption lines of cold gases.

To further decrease the likelihood that the composition will degrade and/or decompose over extended periods of time, the composition should avoid, when feasible: excessive exposure to direct sunlight, excessive heat and/or elevated temperatures. As such, in specific embodiments, the enclosed container of the kit can include printed indicia, with instructions to avoid excessive heat, elevated temperatures, direct sunlight, or a combination thereof.

Over extended periods of time, hydrogen peroxide and/or peracetic acid present in the composition will be susceptible to degrade or decompose (and a portion of the hydrogen peroxide may degrade or decompose), thereby evolving oxygen.

In specific embodiments, the enclosed container includes a head space, pressure valve, or combination thereof. In specific embodiments, the enclosed container includes a pressure valve, configured to release excessive gas from within the enclosed container. The presence of a head space and pressure valve in the container will allow for the escape of gas (e.g., oxygen) from the enclosed container, without the likelihood that the container will explode from the elevated pressure that would otherwise develop.

The term "head space" refers to a portion of the inside of a container that is not occupied by the liquid contents of the container. In particular, when a container includes a liquid composition, a head space can be present in the container such that a portion of the inside of the container does not include liquid composition, but instead includes a gas or vacuum. In specific embodiments, the head space can include oxygen ($O_2$), peracetic acid and/or acetic acid vapor. In further specific embodiments, the head space can be present in up to about 20% (v/v) of the inside of the enclosed container.

The term "pressure valve" refers to a mechanical device that will permit for the passage of gas and not fluid, preferably in one direction only, for example, exiting a container housing the pressure valve, and not entering the container.

The composition of the present invention can be used to effectively reduce the number of microbes located upon a substrate. In specific embodiments, the composition can effectively kill and/or inhibit a microorganism (e.g., virus, fungus, mold, slime mold, algae, yeast, mushroom and/or bacterium), thereby disinfecting or sterilizing the substrate.

In additional specific embodiments, the composition can effectively sanitize a substrate, thereby simultaneously cleaning and disinfecting and/or sterilizing the substrate. In additional specific embodiments, the composition can effectively kill or inhibit all forms of life, not just microorganisms, thereby acting as a biocide.

In specific embodiments, the composition can effectively disinfect or sterilize a substrate. In further specific embodiments, the composition can effectively disinfect or sterilize the surface of a substrate. In additional specific embodiments, the composition can effectively sterilize a substrate. In further specific embodiments, the composition can effectively sterilize the surface of a substrate.

The term "microbe," "microbes" "microorganism," or "micro-organism" refers to a microscopic organism that comprises either a single cell (unicellular), cell clusters, or no cell at all (acellular). Microorganisms are very diverse; they include bacteria, fungi, archaea, and protists; microscopic plants (green algae); and animals such as plankton and the planarian. Some microbiologists also include viruses, but others consider these as non-living. Most microorganisms are unicellular (single-celled), but this is not universal, since some multicellular organisms are microscopic, while some unicellular protists and bacteria, like *Thiomargarita namibiensis*, are macroscopic and visible to the naked eye.

The term "virus" refers to a small infectious agent that can replicate only inside the living cells of organisms. Virus particles (known as virions) consist of two or three parts: the genetic material made from either DNA or RNA, long molecules that carry genetic information; a protein coat that protects these genes; and in some cases an envelope of lipids that surrounds the protein coat when they are outside a cell. The shapes of viruses range from simple helical and icosahedral forms to more complex structures. The average virus is about one one-hundredth the size of the average bacterium. An enormous variety of genomic structures can be seen among viral species; as a group they contain more structural genomic diversity than plants, animals, archaea, or bacteria. There are millions of different types of viruses, although only about 5,000 of them have been described in detail. A virus has either DNA or RNA genes and is called a DNA virus or a RNA virus respectively. The vast majority of viruses have RNA genomes. Plant viruses tend to have single-stranded RNA genomes and bacteriophages tend to have double-stranded DNA genomes.

The term "fungi" or "fungus" refers to a large and diverse group of eucaryotic microorganisms whose cells contain a nucleus, vacuoles, and mitochondria. Fungi include algae, molds, yeasts, mushrooms, and slime molds. See, Biology of Microorganisms, T. Brock and M. Madigan, 6th Ed., 1991, Prentice Hill (Englewood Cliffs, N.J.). Exemplary fungi include Ascomycetes (e.g., *Neurospora, Saccharomyces, Morchella*), Basidiomycetes (e.g., *Amanita, Agaricus*), Zygomycetes (e.g., *Mucor, Rhizopus*), Oomycetes (e.g., *Allomyces*), and Deuteromycetes (e.g., *Penicillium, Aspergillus*).

The term "mold" refers to a filamentous fungus, generally a circular colony that may be cottony, wooly, etc. or glabrous, but with filaments not organized into large fruiting bodies, such as mushrooms. See, e.g., Stedman's Medical Dictionary, 25th Ed., Williams & Wilkins, 1990 (Baltimore, Md.). One exemplary mold is the Basidiomycetes called wood-rotting fungi. Two types of wood-rotting fungi are the white rot and the brown rot. An ecological activity of many fungi, especially members of the Basidiomycetes is the decomposition of wood, paper, cloth, and other products derived from natural sources. Basidiomycetes that attack these products are able to utilize cellulose or lignin as carbon and energy sources. Lignin is a complex polymer in which the building blocks are phenolic compounds. It is an important constituent of woody plants. The decomposition of lignin in nature occurs almost exclusively through the agency of these wood-rotting fungi. Brown rot attacks and decomposes the cellulose and the lignin is left unchanged. White rot attacks and decomposes both cellulose and lignin. See, Biology of Microorganisms, T. Brock and M. Madigan, 6th Ed., 1991, Prentice Hill (Englewood Cliffs, N.J.).

The term "slime molds" refers to nonphototrophic eucaryotic microorganisms that have some similarity to both fungi and protozoa. The slime molds can be divided into two groups, the cellular slime molds, whose vegetative forms are composed of single amoebalike cells, and the acellular slime molds, whose vegetive forms are naked masses of protoplasms of indefinite size and shape called plasmodia. Slime molds live primarily on decaying plant matter, such as wood, paper, and cloth. See, Biology of Microorganisms, T. Brock and M. Madigan, 6th Ed., 1991, Prentice Hill (Englewood Cliffs, N.J.).

The term "algae" refers to a large and diverse assemblage of eucaryotic organisms that contain chlorophyll and carry out oxygenic photosynthesis. See, Biology of Microorganisms, T. Brock and M. Madigan, 6th Ed., 1991, Prentice Hill (Englewood Cliffs, N.J.). Exemplary algae include Green Algae (e.g., *Chlamydomonas*), Euglenids (e.g., *Euglena*), Golden Brown Algae (e.g., Navicula), Brown Algae (e.g., *Laminaria*), Dinoflagellates (e.g., Gonyaulax), and Red Algae (e.g., Polisiphonia).

The term "yeast" refers to unicellular fungi, most of which are classified with the Ascomytes. See, Biology of Microorganisms, T. Brock and M. Madigan, 6th Ed., 1991, Prentice Hill (Englewood Cliffs, N.J.).

The term "mushrooms" refer to filamentous fungi that are typically from large structures called fruiting bodies, the edible part of the mushroom. See, Biology of Microorganisms, T. Brock and M. Madigan, 6th Ed., 1991, Prentice Hill (Englewood Cliffs, N.J.).

The term "bacterium" or "bacteria" refers to a large domain of prokaryotic microorganisms. Typically a few micrometers in length, bacteria have a wide range of shapes, ranging from spheres to rods and spirals. Bacteria are present in most habitats on Earth, growing in soil, acidic hot springs, radioactive waste, water, and deep in the Earth's crust, as well as in organic matter and the live bodies of plants and animals, providing outstanding examples of mutualism in the digestive tracts of humans, termites and cockroaches. There are typically about 40 million bacterial cells in a gram of soil and a million bacterial cells in a milliliter of fresh water; in all, there are approximately five nonillion ($5\times10^{30}$ bacteria on Earth, forming a biomass that exceeds that of all plants and animals. Most bacteria have not been characterized, and only about half of the phyla of bacteria have species that can be grown in the laboratory.

The term "*P. aeruginosa*" or "*Pseudomonas aeruginosa*" refers to a common bacterium that can cause disease in animals, including humans. It is found in soil, water, skin flora, and most man-made environments throughout the world. It thrives not only in normal atmospheres, but also in hypoxic atmospheres, and has, thus, colonized many natural and artificial environments. It uses a wide range of organic material for food; in animals, the versatility enables the organism to infect damaged tissues or those with reduced immunity. The symptoms of such infections are generalized inflammation and sepsis. If such colonizations occur in critical body organs, such as the lungs, the urinary tract, and kidneys, the results can be fatal. Because it thrives on most surfaces, this bacterium is also found on and in medical equipment, including catheters, causing cross-infections in hospitals and clinics. It is implicated in hot-tub rash.

The term "*S. aureus*" or "*Staphylococcus aureus*" refers to a facultative anaerobic Gram-positive bacterium. It is frequently found as part of the normal skin flora on the skin and nasal passages. It is estimated that 20% of the human population are long-term carriers of *S. aureus*. *S. aureus* is the most common species of staphylococci to cause Staph infections. The reasons *S. aureus* is a successful pathogen are a combination host and bacterial immuno-evasive strategies. One of these strategies is the production of carotenoid pigment staphyloxanthin which is responsible for the characteristic golden color of *S. aureus* colonies. This pigment acts as a virulence factor, primarily being a bacterial antioxidant which helps the microbe evade the host's immune system in the form of reactive oxygen species which the host uses to kill pathogens.

*S. aureus* can cause a range of illnesses from minor skin infections, such as pimples, impetigo, boils (furuncles), cellulitis folliculitis, carbuncles, scalded skin syndrome, and abscesses, to life-threatening diseases such as pneumonia, meningitis, osteomyelitis, endocarditis, toxic shock syndrome (TSS), bacteremia, and sepsis. Its incidence is from skin, soft tissue, respiratory, bone, joint, endovascular to wound infections. It is still one of the five most common causes of nosocomial infections, often causing postsurgical wound infections. Each year, some 500,000 patients in American hospitals contract a staphylococcal infection.

Methicillin-resistant *S. aureus*, abbreviated MRSA and often pronounced "mer-sa" (in North America), is one of a number of greatly-feared strains of *S. aureus* which have become resistant to most antibiotics. MRSA strains are most often found associated with institutions such as hospitals, but are becoming increasingly prevalent in community-acquired infections.

The term "*E. hirae*" or "*Enterococcus hirae*" refers to a species of *Enterococcus.*

The term "*M. terrae*" or "*Mycobacterium terrae*" refers to a slow-growing species of *Mycobacterium*. It is an ungrouped member of the third Runyon (nonchromatogenic mycobacteria). It is known to cause serious skin infections, which are relatively resistant to antibiotic therapy. Joints, tendons, lung, gastrointestinal tract, and genitourinary tract can be infected by *Mycobacterium terrae.*

The term "*Mycobacterium avium* complex," "*M. avium* complex" or "MAC" refers to a group of genetically related bacteria belonging to the genus *Mycobacterium*. It includes *Mycobacterium avium* and *Mycobacterium intracellulare.*

The term "*M. avium*" or "*Mycobacterium avium*" refers to a species of *Mycobacterium.*

The term "*M. intracellulare*" or "*mycobacterium intracellulare*" refers to a species of *Mycobacterium.*

*Clostridium difficile* (*C. difficile*), a Gram-positive bacterium, also known in the art as *Clostridioides difficle*, is the leading cause of antibiotic-associated diarrhea and pseudomembranous colitis.

The compositions described herein are able to kill *C. difficile* (6 log) within 3 minutes, *B. atropheau* (6 log) within 1 minute and/or *M. terrae* (6 log) within 1 minute.

The compositions are non-corrosive (brass corrosion rate of 0.07 mg/minute or less) and/or nor corrosive effect(s) with aluminum or stainless steel (304).

The compositions described herein are stable for at least 1 year at room temperature and pressure and have a low odor(s), such as acetic acid.

The following paragraphs enumerated consecutively from 1 through 48 provide for various aspects of the present invention. In one embodiment, in a first paragraph (1), the present invention provides a composition comprising: hydrogen peroxide; a first organic acid comprising a $C_1$ to a $C_6$ monocarboxylic acid; a second organic acid comprising one or more of an alpha hydroxy acid, a beta hydroxy acid, a $C_2$ to a $C_6$ alkyl or alkylene dicarboxylic acid, an aromatic dicarboxylic acid, a reductone or a heteroaromatic monocarboxylic acid; a third organic acid comprising a heteroaromatic dicarboxylic or heteroaromatic tricarboxylic acid; a fatty acid; and a surfactant.

2. The composition according to paragraph 1, wherein the hydrogen peroxide concentration is about 0.5 wt. % to about 40 wt. %.

3. The composition according to paragraph 2, wherein the hydrogen peroxide concentration is about 4 wt. % to about 10 wt. %.

4. The composition according to any of paragraphs 1 to 3, wherein the first organic acid concentration is about 1 wt. % to about 55 wt. %.

5. The composition according to paragraph 4, wherein the first organic acid concentration is about 0.1 wt. % to about 8 wt. %.

6. The composition according to paragraph 1, wherein the first organic acid comprises acetic acid.

7. The composition according to any of paragraphs 1 through 4, wherein the second organic acid concentration is about 0.5 wt. % to about 10 wt. %.

8. The composition according to any of paragraphs 1 through 7, wherein the alpha hydroxy acid comprises glycolic acid, lactic acid, citric acid, malic acid, tartaric acid.

9. The composition according to any of paragraphs 1 through 7, wherein the beta hydroxy acid comprises salicylic acid, beta hydroxybutanoic acid, tropic acid, or trethocanic acid.

10. The composition according to any of paragraphs 1 through 7, wherein the $C_2$ to a $C_6$ alkyl or alkylene dicarboxylic acid comprises oxalic acid, malonic acid, succinic acid, glutaric acid, adipic acid, maleic acid, itaconic acid, citraconic acid, mesaconic acid, muconic acid or fumaric acid.

11. The composition according to any of paragraphs 1 through 7, wherein the aromatic dicarboxylic acid comprises phthalic acid, isophthalic acid, terephthalic acid.

12. The composition according to any of paragraphs 1 through 7, wherein the reductone comprises ascorbic acid.

13. The composition according to any of paragraphs 1 through 7, wherein the heteroaromatic monocarboxylic acid is picolinic acid.

14. The composition according to paragraph 8, wherein the alpha hydroxy acid comprises citric acid.

15. The composition according to any of paragraphs 1 through 14, wherein the third organic acid concentration is about 0.1 wt. % to about 1 wt. %.

16. The composition according to paragraph 15, wherein the third organic acid concentration is about 0.1 wt. % to about 0.5 wt. %.

17. The composition according to any of paragraphs 1 through 16, wherein heteroaromatic dicarboxylic acid comprises a dipiconilic acid.

18. The composition according to any of paragraphs 1 through 17, wherein the fatty acid concentration is about 0.01 wt. % to about 5 wt. %.

19. The composition according to paragraph 18, wherein the fatty acid concentration is about 0.1 wt. % to about 5 wt. %.

20. The composition according to any of paragraphs 1 through 19, wherein the fatty acid comprises a short chain fatty acid, a medium chain fatty acid, a long chain fatty acid, a very long chain fatty acid, a saturated fatty acid or an unsaturated fatty acid.

21. The composition according to paragraph 20, wherein the fatty acid is a medium chain saturated fatty acid having a carbon chain length of $C_6$ to $C_{12}$.

22. The composition according to paragraph 21, wherein the medium chain saturated fatty acid is decanoic acid.

23. The composition according to any of paragraphs 1 through 22, wherein the surfactant concentration is about 0.1 wt. % to about 10 wt. %.

24. The composition according to paragraph 23, wherein the surfactant concentration is about 0.1 wt. % to about 5 wt. %.

25. The composition according to any of paragraphs 1 through 24, wherein the surfactant comprises an alkyl sulfate salt.

26. The composition according to paragraph 25, wherein the alkyl sulfate salt is sodium dodecyl sulfate.

27. The composition according to paragraph 1, wherein hydrogen peroxide is present, the first organic acid comprises acetic acid, the second organic acid comprises citric acid, the third organic acid comprises a dipicolinic acid, the fatty acid comprises decanoic acid and the surfactant is sodium dodecyl sulfate.

28. The composition according to paragraph 27, wherein the hydrogen peroxide concentration is about 4 wt. % to about 10 wt. %, the acetic acid concentration is about 0.1 wt. % to about 8 wt. %, the citric acid concentration is about 0.5 wt. % to about 10 wt. %, the dipicolinic acid concentration is about 0.1 wt. % to about 0.5 wt. %, the decanoic acid concentration is about 0.01 wt. % to about 5 wt. % and the sodium dodecyl sulfate concentration is about 0.1 wt. % to about 5 wt. %.

29. The composition according to any of paragraphs 1 through 28, wherein a solvent is present.

30. The composition according to paragraph 29, wherein the solvent is water.

31. The composition according to either paragraph 29 or 30, wherein the solvent or water is present to provide a total composition of 100 wt. %.

32. The composition according to any of paragraphs 1 through 31, wherein the composition is a liquid concentrate disinfectant or sterilant.

33. The composition according to paragraphs 1 through 31, wherein the composition is formulated for use in a sprayable composition.

34. The composition according to paragraphs 1 through 31, wherein the composition is formulated for use with a wipe.

35. The composition according to any of paragraphs 1 through 31, wherein the composition does not include 1-hydroxyethylidene-1,1-diphosphonic acid.

36. The composition according to any of paragraphs 1 through 31, wherein the composition further comprises 1-hydroxyethylidene-1,1-diphosphonic acid.

37. The composition according to paragraphs 1 through 36, wherein the composition is formulated for use in contacting a surface of at least one of a hospital, physician's office, medical clinic, medical facility, dental office, dental facility, airport, school, pet store, zoo, children's day care, elderly nursing home, museum, movie theatre, athletic facility, sporting arena, gymnasium, rest room, bathroom, shopping center, amusement park, church, synagogue, mosque, temple, restaurant, food processing facility, food manufacturing facility, pharmaceutical company, hot-tub, sauna, and clean room.

38. The composition according to paragraphs 1 through 36, wherein the composition is formulated for use in contacting at least one of metal, plastic, natural rubber, synthetic rubber, glass, stone, grout, fiberglass, wood, concrete, construction product, and building product.

39. The composition according to paragraphs 1 through 36, wherein the composition is formulated for use in contacting at least one of medical equipment, medical device, surface in the medical industry, dental equipment, dental device, and surface in the dental industry.

40. The composition according to paragraph 39, wherein the medical device is an endoscope.

41. A method for reducing the number of microbes located upon a substrate, the method comprising the step of contacting the substrate with an effective amount of the composition according to any of paragraphs 1 through 36 for a sufficient period of time, effective to reduce the number of microbes located upon the substrate.

42. The method according to paragraph 41, wherein the microbe includes at least one of a virus, fungus, mold, slime mold, algae, yeast, mushroom and bacterium.

43. The method according to paragraph 41, wherein up to about 4 logs of the microbe is inactivated in about 15 minutes, or less.

44. A method of killing or inhibiting a microorganism, the method comprising the step of contacting the microorganism with an antimicrobially effective amount of the composition according to any of paragraphs 1 through 36, for a sufficient period of time, effective to kill or inhibit the microorganism.

45. A method of disinfecting or sterilizing a substrate, the method comprising the step of contacting the substrate with an effective amount of the composition according to any of paragraphs 1 through 36, for a sufficient period of time, effective to disinfect or sterilize the substrate.

46. The method according to paragraph 41, wherein the substrate to be contacted is a medical device.

47. The method according to paragraph 41, wherein the substrate to be contacted is a soiled endoscopic device.

48. The method according to paragraph 41, wherein the substrate to be contacted is cleaned prior to disinfecting or sterilization.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

Examples

Unless otherwise stated, the remainder of the compositions described herein are made up with water to achieve 100 wt. %. The $H_2O_2$ (hydrogen peroxide) used was a commercial 50% concentrate in water.

In the following Formulae, #17 refers to Formula 17 described below.

A series of compositions were prepared according to the following components by weight percent.

1. 10% $H_2O_2$, 4% Glutaric Acid
2. 6% $H_2O_2$, 8% Glutaric Acid
3. 10% $H_2O_2$, 8% Glutaric Acid
7. 10% $H_2O_2$, 4% Citric Acid, 0.3% Phosphoric Acid
9. 10% $H_2O_2$, 8% Citric Acid, 0.3% Phosphoric Acid
10. 10% $H_2O_2$, 8% Citric Acid
11. 10% $H_2O_2$, 8% Citric Acid, 0.3% Amberlite
17. 10% $H_2O_2$, 1.5% Acetic Acid, 0.5% Citric Acid
18. 10% $H_2O_2$, 2% Acetic Acid, 0.5% Dequest
23. 10% $H_2O_2$, 1.5% Acetic Acid, 0.5% Citric Acid+0.3% Dequest (=#17+Dequest)
24. 10% $H_2O_2$, 1.5% Acetic Acid, 0.25% Citric Acid+0.25% Na-Citrate (=#17+sodium citrate)
25. 10% $H_2O_2$, 1.5% Acetic Acid, 0.5% Citric Acid+0.1% dipicolinic (=#17+dipicolinic)
26. 10% $H_2O_2$, 1.5% Acetic Acid, 0.25% Citric Acid+0.1% dipicolinic+0.2% SDS+0.25% Na-citrate+0.05% decanoic (=#17+dipicolinic+SDS+citrate+decanoic)
27. 10% $H_2O_2$, 1.5% Acetic Acid, 0.5% Citric Acid+0.1% dipicolinic+0.2% SDS+0.05% decanoic (=#17+dipicolinic+SDS+decanoic)
29. 10% $H_2O_2$, 0.2% Acetic Acid, 1% Citric Acid
30. 10% $H_2O_2$, 0.1% Acetic Acid, 1% Citric Acid
31. 10% $H_2O_2$, 2% Acetic Acid, 1% Citric Acid
33. 10% $H_2O_2$, 1% Acetic Acid, 0.5% Citric Acid
34. 10% $H_2O_2$, 0.8% Acetic Acid, 0.5% Citric Acid
35. 10% $H_2O_2$, 0.5% Acetic Acid, 0.5% Citric Acid
36. 15% $H_2O_2$, 0.8% Acetic Acid, 0.5% Citric Acid
37. 10% $H_2O_2$, 0% Acetic Acid, 1% Citric Acid
38. 10% $H_2O_2$, 0.5% Acetic Acid, 0.8% Citric Acid (Add Acetic at the end of brewing, not brewing Acetic)
39. 10% $H_2O_2$, 0.5% Acetic Acid, 0.5% Citric Acid (Add Acetic at the end of brewing)
40. 10% $H_2O_2$, 0.5% Acetic Acid, 0.3% Citric Acid (Add Acetic at the end of brewing)
41. 10% $H_2O_2$, 0.15% Acetic Acid, 1% Citric Acid (Add Acetic at the end of brewing)
42. 10% $H_2O_2$, 1% Propionic Acid (brew for 24 hrs. then add DI, deionized water)
43. 10% $H_2O_2$, 1% Propionic Acid, 0.5% Acetic Acid (brew for 24 hrs. then add DI)
44. 10% $H_2O_2$, 0.5% Acetic Acid, 0.8% Citric Acid (normal brewing both PAA and PCA)
45. 10% $H_2O_2$, 0.5% Acetic Acid, 0.5% Citric Acid (normal brewing both PAA and PCA)
46. 10% $H_2O_2$, 0.5% Acetic Acid, 0.3% Citric Acid (normal brewing both PAA and PCA)
47. 10% $H_2O_2$, 0.15% Acetic Acid, 1% Citric Acid (normal brewing both PCA and PAA)
101. 6% $H_2O_2$, 2% Benzoic Acid
102. 6% $H_2O_2$, 2% Salicylic Acid
103. 6% $H_2O_2$, 2% P-Anisic Acid
104. 6% $H_2O_2$, 2% Succinic Acid
105. 6% $H_2O_2$, 2% Maleic Acid
106. 6% $H_2O_2$, 2% Phenoxyacetic Acid
107. 6% $H_2O_2$, 2% Gluconic Acid
108. 6% $H_2O_2$, 2% Ascorbic Acid
109. 6% $H_2O_2$, 2% 1,3,5-Benzentricarboxylic Acid
110. 6% $H_2O_2$, 2% Picolinc Acid
111. 6% $H_2O_2$, 2% Malonic Acid
112. 6% $H_2O_2$, 7% Malonic Acid "Normal brew" is achieved by adding all components in the formulation including water to generate the peracid of interest. This is differentiated over "fast brew" conditions where acceleration of the generation of the peracid is achieved by allowing components to react with water added after about 24 hours.

Formula 27: 10% $H_2O_2$, 1.5% Acetic Acid, 0.5% Citric Acid+0.1% dipicolinic+0.2% SDS+0.05% decanoic (equivalent to formula 17 (See below)+dipicolinic+SDS+decanoic)

Corrosion rate against brass: 0.070 mg/min.

Residual (% Remain): 0.926%.

Other variations that were tested:

Formula 17: 10% $H_2O_2$, 1.5% Acetic Acid, 0.5% Citric Acid

Corrosion rate against brass: 0.366 mg/min.

This formulation showed good micro efficacy against spores with complete kill at 5 min and 10 min.

Due to the higher corrosion rate, the formulation was further modified with the anti-corrosion package (Decanoic and SDS)

Formula 18: 10% $H_2O_2$, 2% Acetic Acid, 0.5% Dequest

This was a higher concentration version of Formulation 17.

Corrosion rate against brass: 0.637 mg/min.

Due to the higher corrosion rate observed compared to Formula 17, the formulation was not further tested.

Formulae 23 to 27: Different corrosion packages

The 5 formulations were made with different type of anti-corrosion packages in view of the corrosive property of Formula 17.

Formula 29: 10% $H_2O_2$, 0.2% Acetic Acid, 1% Citric Acid

Formula 30: 10% $H_2O_2$, 0.1% Acetic Acid, 1% Citric Acid

Both Formula 29 and 30 did not achieve good micro efficacy due to the low acetic acid (aka PAA concentration at equilibrium). The results indicated that the peracetic acid (PAA) were more important for the micro efficacy than the citric acid.

Formula 31: 10% $H_2O_2$, 2% Acetic Acid, 1% Citric Acid

Good micro efficacy was observed with >6 log reduction at 3 minutes contact time.

Formula 33: 10% $H_2O_2$, 1% Acetic Acid, 0.5% Citric Acid

Formula 34: 10% $H_2O_2$, 0.8% Acetic Acid, 0.5% Citric Acid

Formula 35: 10% $H_2O_2$, 0.5% Acetic Acid, 0.5% Citric Acid

Formula 36: 15% $H_2O_2$, 0.8% Acetic Acid, 0.5% Citric Acid

Formulations 33 to 36 against *B. atrophaeus* showed good efficacy with 5 minutes contact time.

Brew methods were also tested, for example, Formulation 38 to 47 showed the different concentration combinations of acetic acid and citric acid but also the different brew method tested as well.

One method was to add the acetic acid after the chemistry was brewed with citric acid only. This would create more percitric acid in comparison to peracetic acid.

Another method was to brew the chemistry with both acetic acid and citric acid added from the beginning of the brew. (This theoretically favored the formation of peracetic acid (PAA) more than percitric acid (PCA)).

| Formula # | Detail | Corrosion Rate (mg/min) | Micro Efficacy |
|---|---|---|---|
| 23 | 10% $H_2O_2$, 1.5% Acetic Acid, 0.5% Citric Acid + 0.3% Dequest (=#17 + Dequest) | 0.480 | 4 log reduction at 7 min contact time |
| 24 | 10% $H_2O_2$, 1.5% Acetic Acid, 0.25% Citric Acid + 0.25% Na-Citrate (=#17 + sodium citrate) | 0.358 | No Data |
| 25 | 10% $H_2O_2$, 1.5% Acetic Acid, 0.5% Citric Acid + 0.1% dipicolinic (=#17 + dipicolinic) | 0.445 | TNTC for up to 7 min contact time. |
| 26 | 10% $H_2O_2$, 1.5% Acetic Acid, 0.25% Citric Acid + 0.1% dipicolinic + 0.2% SDS + 0.25% Na-citrate + 0.05% decanoic (=17 + dipicolinic + SDS + citrate + decanoic) | 0.044 | No Data |
| 27 | 10% $H_2O_2$, 1.5% Acetic Acid, 0.5% Citric Acid + 0.1% dipicolinic + 0.2% SDS + 0.05% decanoic (=17 + dipicolinic + SDS + decanoic) | 0.070 | Achieve greater than 6 log reduction of *C. diff* at 3 min contact time. |

TNTC denotes "too numerous to count"

Concentration ranges tested for combination of acetic acid and citric acid.

Formula 4: 10% $H_2O_2$, 1% Acetic Acid, 1% Citric Acid

Formula 5: 6% $H_2O_2$, 2% Acetic Acid, 1% Citric Acid

Formula 6: 10% $H_2O_2$, 2% Acetic Acid, 1% Citric Acid

Formulae 4 to 6 were tested against *B. atrophaeus* with acceptable results with ≥6 log reductions at 3 to 5 minutes of contact time.

Formula 17: 10% $H_2O_2$, 1.5% Acetic Acid, 0.5% Citric Acid

Formula 17 had similar micro efficacy against *C. diff* with good micro efficacy of 5 minutes or but had an increased corrosion rate. Therefore, the formulation was further developed to Formula 27.

Results against *B. atrophaeus* showed better efficacy after brewing having both acetic acid and citric acid added at the beginning of the brew due to the higher PAA concentration achieved at equilibrium.

Stability Study

For Formula 27, the stability of nine different manufactured lots of the *C. diff* surface disinfectant were tested for up to 18 months. (Lot EWR 1602-1, 2, and 3, and Lot EWR 1631-1, 2, and 3 and Lot EWR 1632-1, 2, and 3).

From the results, all nine lots demonstrated good stability over 18 months at 25±2° C. and 60±5% RH. The results passed the criteria for the stability set for the study (PAA between 0.10 to 0.22%) with all nine lots ended at 18 months with PAA ranged between 0.17 to 0.21% PAA for the stability study. See FIGS. 1 through 5.

Stability of Formula 27 on a Wipe.

The wipe material was made of polypropylene. The wipe was prepared by adding the chemistry solution directly into a container that held the pre-cut wipes and allowed the wipes to soak up the chemistry. The wipes were kept at ambient temperature (20-27° C.) with humidity equivalent to the room (estimated to be between 40-60% RH). Formulae 27A, 27B, 27C and 27 Control all were the same chemistry and were different lots of materials.

Figure 6:
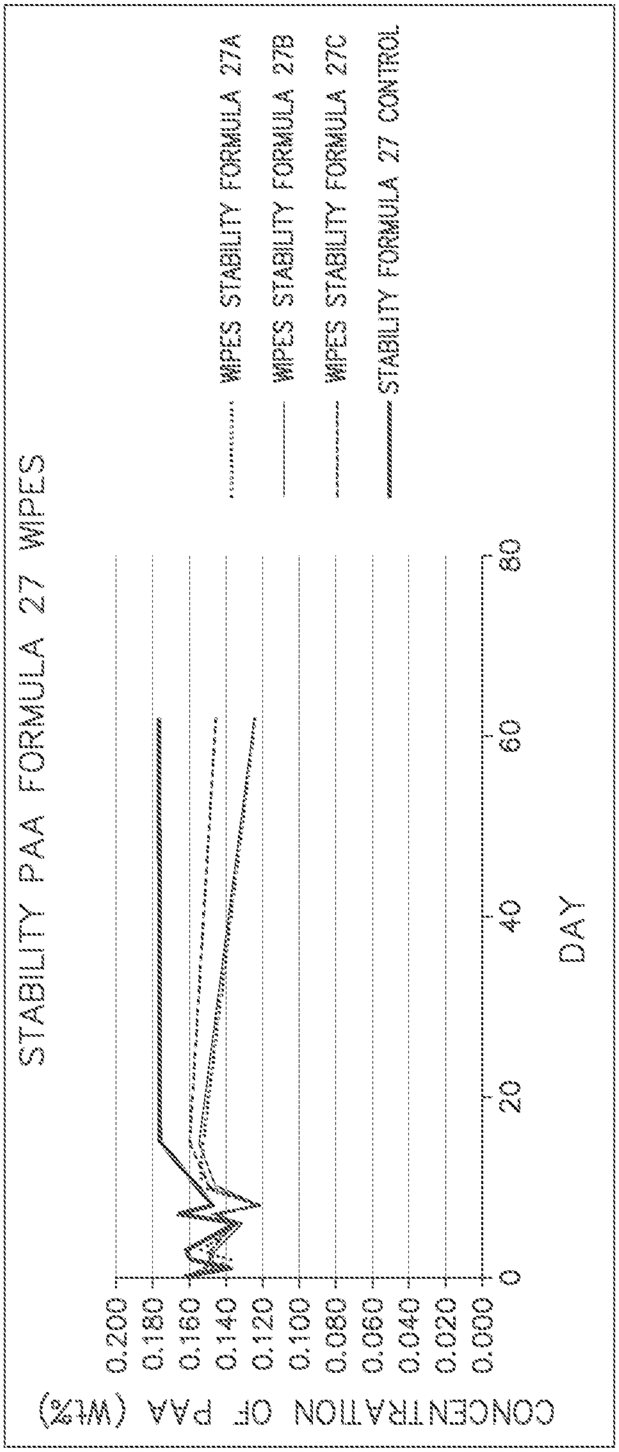
FIG. 6 demonstrates hydrogen peroxide stability data for Formulation 27 added to wipes over a period of time.
Figure 7:
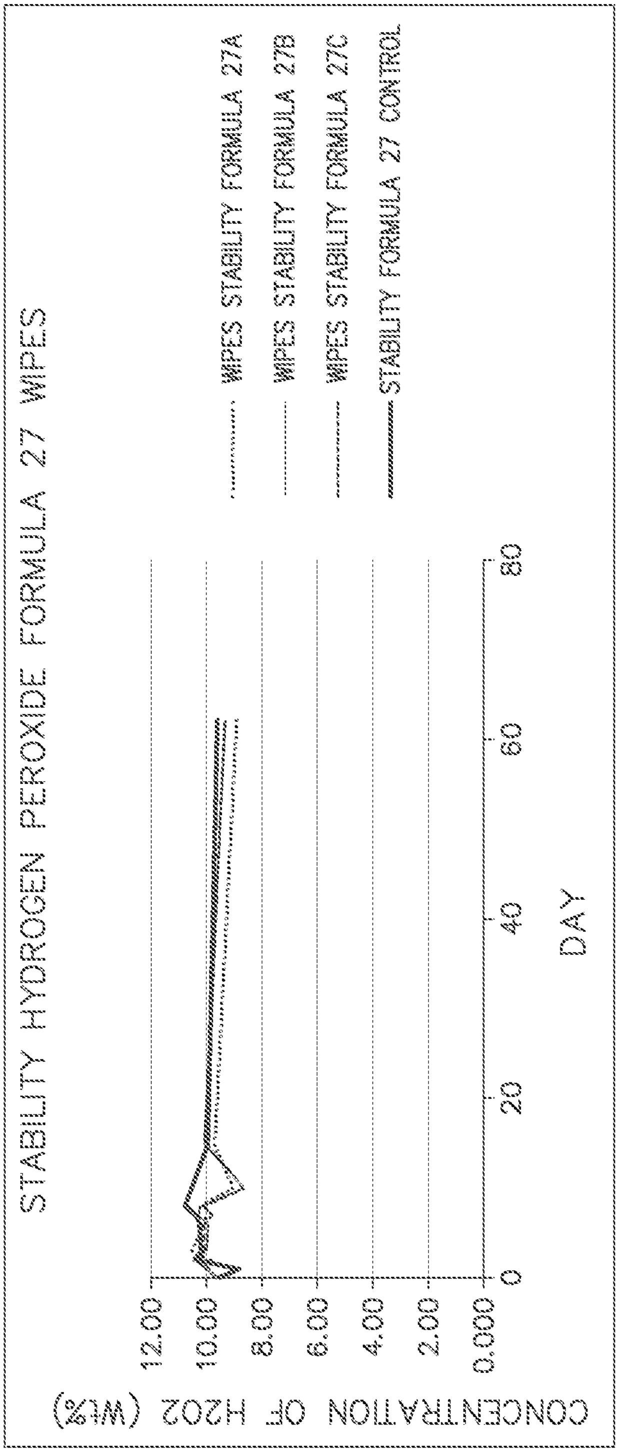
FIG. 7 demonstrates peracetic acid stability data for Formulation 27 added to wipes over a period of time.

The study was performed for up to 62 days which provided feasibility results for the stability of the PAA composition. See FIGS. 6 and 7.

Stress Data for Formula 27 (for Reuse HLD Chemistry)

The chemistry was stressed following the procedure for Re-Use Chemistry stressing to simulate the exposure to bio-burden and equipment exposure.

The study was performed for up to 21 days and the data showed good feasibility results up to 10 days with approximately only a 30% loss of PAA.

Figure 8:
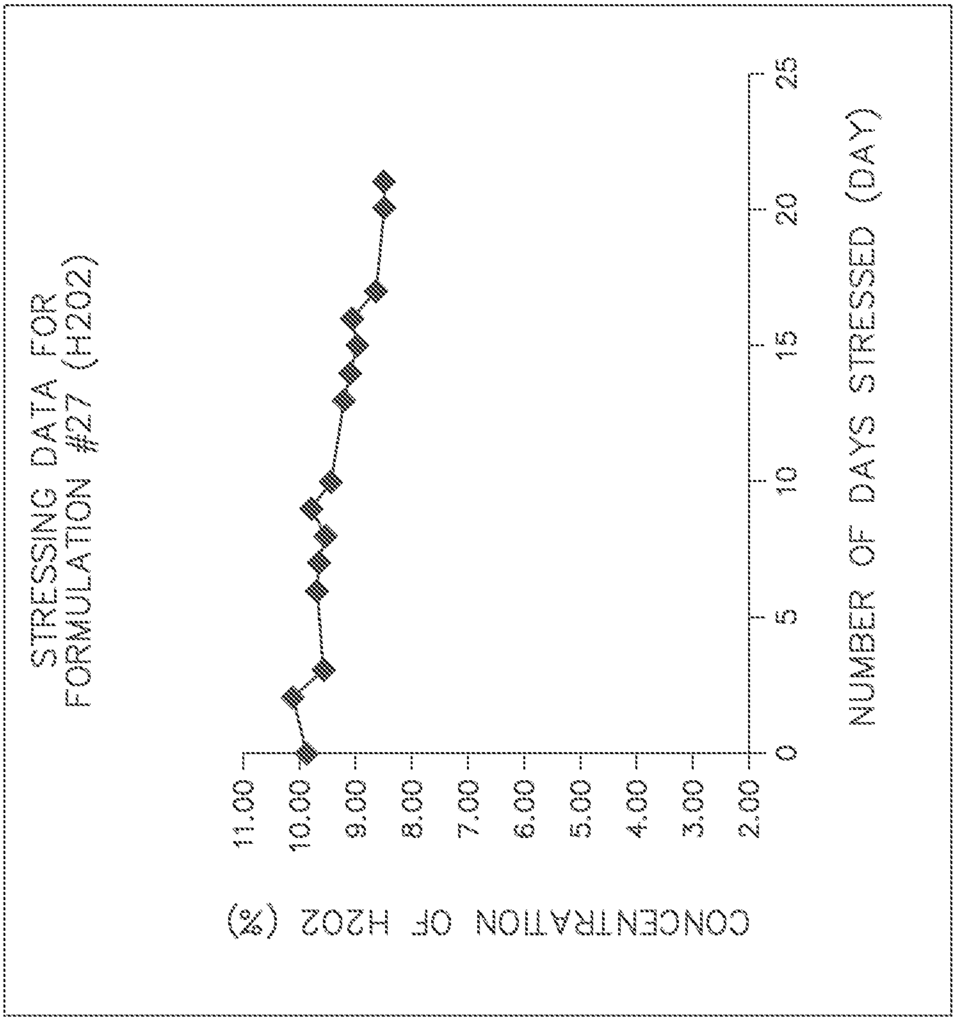
FIG. 8 provides stress data for Formulation 27 for hydrogen peroxide concentration.
Figure 9:
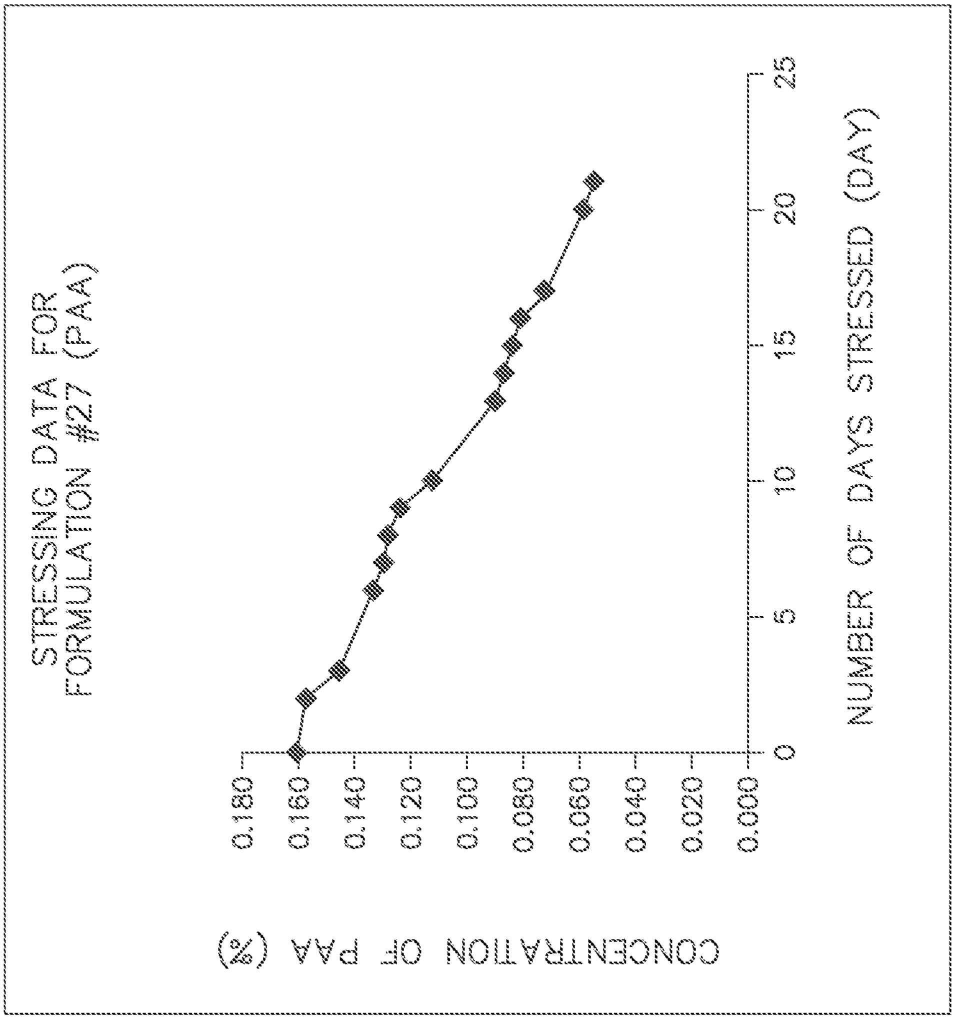
FIG. 9 provides stress data for Formulation 27 for peracetic acid concentration.

From the test data, the chemistry was still able to show acceptable micro efficacy at 70% of its strength which was what was used to base the result of the stress study on. See FIGS. 8 and 9.

"Re-Use Chemistry" is defined as a chemistry that can be used to disinfect medical devices multiple times before the chemistry needs to be discarded. A comparative is Cantel product Rapicide OPA/28, which has a claim that allows the chemistry to be re-used for High Level Disinfection of endoscopes for up to 28 days before the chemistry loses its effectiveness to disinfect the endoscope. Similar to Rapicide OPA/28, Formulation 27 can also be used to disinfect medical devices multiple time before it loses its effectiveness.

Stressing Procedure 1 gallon of germicide was placed in a suitable container.

Hard water was added to provide a concentration of 400 ppm of germicide. The hard water was prepared as in the AOAC International Official Methods of Analysis (2000) Chapter 6, page 11, section "E", synthetic hard water. The synthetic hard water was prepared as follows:

Prepare Solution 1 by dissolving 31.74 g $MgCl_2$ (or equivalent of hydrates) and 73.99 g $CaCl_2$) in boiled distilled $H_2O$ and diluting to 1 L. Prepare Solution 2 by dissolving 56.03 g $NaHCO_3$ in boiled distilled $H_2O$ and diluting to 1 L. Solution 1 may be heat sterilized; Solution 2 must be sterilized by filtration. Place required amount Solution 1 in sterile 1 L flask and add >600 mL sterile distilled $H_2O$; then add 4 mL Solution 2 and dilute to 1 L with sterile distilled $H_2O$. Each mL Solution 1 will give a water equivalent to ca 100 ppm of hardness calculated as $CaCO_3$ by formula:

$$\text{Total hardness as ppm } (\mu g/mL)\ CaCO_3 = 2.495 \times \text{ppm } (\mu g/mL)\ Ca + 4.115 \times \text{ppm } (\mu g/mL)\ Mg.$$

pH of all test waters <2000 ppm (μg/mL) hardness should be 7.6-8.0. Check prepared synthetic waters chemically for hardness at time of tests, using following hardness method or other methods described in APHA, Standard Methods for the Examination of Water and Wastewater 20th Ed., 1998.

The germicide was stressed with 1 set of inhalation therapy equipment. For one gallon, the respiratory equipment will be comprised of:

1 rebreather bag, split in half;

1 air hose, split in half; and 1 face mask.

The respiratory equipment was prepared and used in the following manner:

The equipment was washed in a detergent solution, the equipment was rinsed with tap water, and drained thoroughly.

The equipment was then soaked in the germicide solution for 5-15 minutes, the equipment was removed and the germicide was drained.

Rinse the equipment. This cycle was repeated 3 times per day of reuse, e.g. 84 cycles for a 28 day reuse test. However more cycles may be scheduled on weekdays to eliminate weekend stressing.

Analysis

The concentration of the active ingredients and the pH of the solution was determined at a defined interval during the stressing. Analyses was conducted at the beginning and end of the stressing period at a minimum.

Acceptable test criteria was based on the concentration of PAA remaining after the stress. The permissible drop of the PAA concentration was down to 70% of the initial concentration. From the data in FIG. 9, it shows that after 10 days of stressing, the chemistry retains 70% of the initial PAA concentration, which was what was defined as acceptable.

Storing the Germicide.

The germicide was stored between stressing procedures at the temperature it was used as disinfectant, e.g., ambient conditions.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A composition comprising:

hydrogen peroxide;

a first organic acid comprising a $C_1$ to a $C_6$ monocarboxylic acid;

a second organic acid comprising one or more of an alpha hydroxy acid, a beta hydroxy acid, a $C_2$ to a $C_6$ alkyl or alkylene dicarboxylic acid, an aromatic dicarboxylic acid, a reductone or a heteroaromatic monocarboxylic acid;

a third organic acid comprising a heteroaromatic dicarboxylic or heteroaromatic tricarboxylic acid; and a corrosion inhibitor package comprising a fatty acid; and a surfactant; wherein the fatty acid, the surfactant, and the heteroaromatic dicarboxylic or heteroaromatic tricarboxylic acid are present in combination and cooperate to reduce corrosion of brass contacted by the composition to a brass corrosion rate of 0.07 mg/minute or less and wherein omission of any one of the fatty acid, the surfactant, or the heteroaromatic dicarboxylic acid results in a corrosion rate greater than 0.07 mg/min.

2. The composition according to claim 1, wherein the first organic acid comprises acetic acid.

3. The composition according to claim 1, wherein the second organic acid concentration is about 0.5 wt. % to about 10 wt. %.

4. The composition according to claim 1, wherein the alpha hydroxy acid comprises glycolic acid, lactic acid, citric acid, malic acid, or tartaric acid.

5. The composition according to claim 1, wherein the beta hydroxy acid comprises salicylic acid, beta hydroxybutanoic acid, tropic acid, or trethocanic acid.

6. The composition according to claim 1, wherein the $C_2$ to a $C_6$ alkyl or alkylene dicarboxylic acid comprises oxalic acid, malonic acid, succinic acid, glutaric acid, adipic acid, maleic acid, itaconic acid, citraconic acid, mesaconic acid, muconic acid or fumaric acid.

7. The composition according to claim 1, wherein the aromatic dicarboxylic acid comprises phthalic acid, isophthalic acid, or terephthalic acid.

8. The composition according to claim 1, wherein the reductone comprises ascorbic acid.

9. The composition according to claim 1, wherein the heteroaromatic monocarboxylic acid is picolinic acid.

10. The composition according to claim 1, wherein the third organic acid concentration is about 0.1 wt. % to about 1 wt. %.

11. The composition according to claim 1, wherein the fatty acid comprises a medium chain fatty acid.

12. The composition according to claim 1, wherein the surfactant comprises an alkyl sulfate salt.

13. The composition according to claim 1, wherein the first organic acid comprises acetic acid, the second organic acid comprises citric acid, the third organic acid comprises a dipicolinic acid, the fatty acid comprises decanoic acid and the surfactant is sodium dodecyl sulfate.

14. The composition according to claim 13, wherein the hydrogen peroxide concentration is about 4 wt. % to about 10 wt. %, the acetic acid concentration is about 0.1 wt. % to about 8 wt. %, the citric acid concentration is about 0.5 wt. % to about 10 wt. %, the dipicolinic acid concentration is about 0.1 wt. % to about 0.5 wt. %, the decanoic acid concentration is about 0.01 wt. % to about 5 wt. % and the sodium dodecyl sulfate concentration is about 0.1 wt. % to about 5 wt. %.

15. The composition according to claim 1, wherein the composition is a liquid concentrate disinfectant or sterilant formulated for repeated reuse in contact with brass-containing medical devices.

16. A method for reducing the number of microbes located upon a substrate, the method comprising the step of contacting the substrate with an effective amount of the composition according to claim 1 for a sufficient period of time, effective to reduce the number of microbes located upon the substrate.

17. The method according to claim 16, wherein up to about 4 logs of the microbe is inactivated in about 15 minutes, or less.

18. A method of killing or inhibiting a microorganism, the method comprising the step of contacting the microorganism with an antimicrobially effective amount of the composition according to claim 1, for a sufficient period of time, effective to kill or inhibit the microorganism.

19. The method according to claim 16, wherein the substrate to be contacted is a medical device.

20. The method according to claim 16, wherein the substrate to be contacted is a soiled endoscopic device.

21. The composition of claim 1, wherein the heteroaromatic dicarboxylic acid comprises dipicolinic acid.

22. The composition of claim 11, wherein the medium-chain saturated fatty acid comprises decanoic acid.

23. The composition of claim 12, wherein the alkyl sulfate salt comprises sodium dodecyl sulfate.

24. The composition of claim 1, wherein the fatty acid is present in an amount of about 0.01 wt. % to about 0.5 wt. %.

25. The composition of claim 1, wherein the surfactant is present in an amount of about 0.1 wt. % to about 1 wt. %.

* * * * *